United States Patent [19]

Olsson et al.

[11] 4,442,300

[45] Apr. 10, 1984

[54] THERAPEUTICALLY ACTIVE COMPOUNDS

[75] Inventors: O. A. Torsten Olsson; Leif Å Svensson, both of Lund; Kjell I. L. Wetterlin, Sandby, all of Sweden

[73] Assignee: Aktiebolaget Draco, Lund, Sweden

[21] Appl. No.: 279,467

[22] Filed: Jul. 1, 1981

[30] Foreign Application Priority Data

Sep. 7, 1980 [GB] United Kingdom ............... 8022440
May 29, 1981 [GB] United Kingdom ............... 8116440

[51] Int. Cl.³ .................. C07C 69/773; C07C 69/88; C07C 69/76
[52] U.S. Cl. ................................ 560/66; 560/72; 560/85; 560/86; 424/307; 424/308
[58] Field of Search .................. 560/66, 72, 85, 86; 424/307, 308

[56] References Cited

FOREIGN PATENT DOCUMENTS 748178 3/1970 Belgium .

Primary Examiner—Paul J. Killos
Attorney, Agent, or Firm—Brumbaugh, Graves, Donohue & Raymond

[57] ABSTRACT

New bronchospasmolytically active compounds exhibiting long duration of action and reduced undesired side effects, of the structural formula

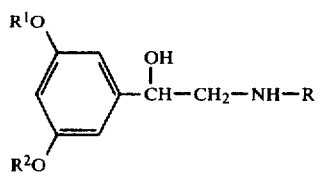

and therapeutically acceptable salts thereof, in which formula R, R¹ and R² are as follows:

R is selected from the group consisting of —C(CH₃)₃,

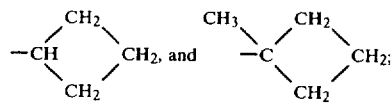

R¹ is selected from the group consisting of H and R²;
R² is selected from the group consisting of (a)

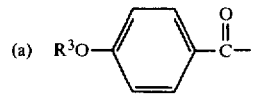

(b)

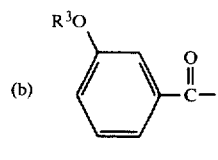

and (c)

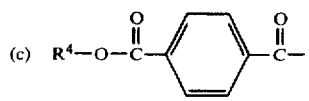

in which formulas
R³ is selected from the group consisting of (a) H;

(b)

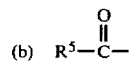

wherein R⁵ is a straight or branched alkyl group containing 1–4 carbon atoms;
and (c)

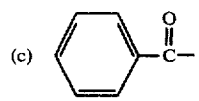

and wherein
R⁴ is selected from the group consisting of
(a) H
(b) an alkyl group containing 1–3 carbon atoms, process for the preparation thereof, chemical intermediates at their preparation, pharmaceutical compositions containing them and their medicinal use.

19 Claims, No Drawings

THERAPEUTICALLY ACTIVE COMPOUNDS

FIELD OF THE INVENTION

The present invention relates to novel compounds having therapeutic activity, to processes for their preparation, to chemical intermediates and their preparation, to pharmaceutical preparations containing them and to the medicinal use of the compounds. In particular, the compounds of the invention have bronchospasmolytic effect and are effective in the treatment of reversible obstructive lung ailments of various genesis, particularly asthmatic conditions. The compounds exhibit a prolonged duration of therapeutic effect and a reduced degree of side effects, especially a reduced heart-stimulating effect. The compounds also exhibit an intrinsic broncho-dilating effect.

BACKGROUND OF THE INVENTION

It is desirable to find bronchodilating agents which have longer duration of activity than the substances which are available on the market. The compound known under the generic name terbutaline, of the structural formula

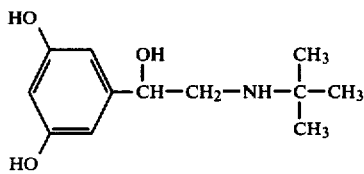

is one of the presently preferred long-acting bronchodilating drugs on the market and which is described i.a. in the U.S. Pat. No. 4,011,258, has a duration of therapeutic activity of about 6 to 8 hours. This duration is confirmed by many years of clinical experience and can be quantified by the finding that a serum concentration of at least about 2 ng/ml of terbutaline is necessary for obtaining the desired therapeutic activity (Hörnblad et al., Europ J. clin Pharmacol. 10 9-18 (1976)).

Another long-acting bronchospasmolytically effective compound available on the market, salbutamol of the stuctural formula

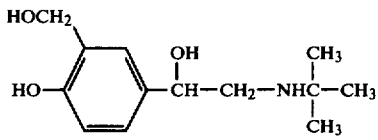

has a duration of bronchospasmolytic activity which is about equal to the duration of terbutaline.

Attempts to obtain bronchospasmolytically active compounds with long duration of activity are reported in the literature. Thus, Zölss, Sci. Pharm. 32 (1964) 2 76–92 discloses i.a. certain esters of ethanol amine derivatives known at that time. Minatoya, The Journal of Pharmacology and Experimental Therapeutics Vol. 206 No. 3, 515–527, discusses the pharmacological properties of a compound known as bitolterol of the formula

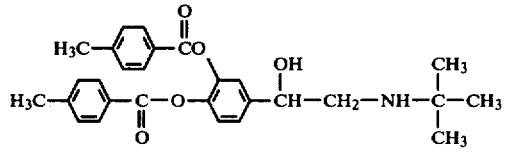

The compound bitolterol which also is disclosed in the Belgian Pat. No. 748 178 proved to have a duration of activity comparable with that of salbutamol.

The problem underlying the present invention was to find orally active bronchospasmolytic agents which have a clinically useful duration of activity of at least 12 hours.

OUTLINE OF THE INVENTION

The present invention provides new compounds having bronchospasmolytic activity at oral administration and exhibiting a duration of activity of up to 12 hours or more. The compounds of the invention, which are mono- or diesters of terbutaline, also exhibit a lower degree of undesired cardiovascular side effects. Thus, they exhibit less chronotropic and inotropic effect than terbutaline. The compounds also exhibit an intrinsic broncho-dilating effect.

The invention also relates to methods for preparation of the compounds, pharmaceutical composition containing the compounds as active ingredients, and to the use of the compounds for therapeutic purposes, in particular the use for producing bronchodilation in mammals including humans. Furthermore, the invention relates to the use of the compounds for producing relaxation of the human uterus, and to pharmaceutical preparations containing the compounds of the invention in combination with a conventionally used bronchodilating agent, as described more in detail below.

DETAILED DESCRIPTION OF THE INVENTION

The invention relates to new compounds of the formula

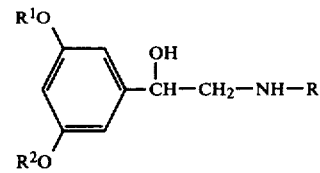

and therapeutically acceptable salts thereof, in which formula R, $R^1$ and $R^2$ are as follows:

R is selected from the group consisting of $-C(CH_3)_3$,

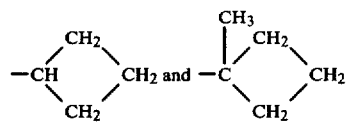

$R^1$ is selected from the group consisting of H and $R^2$,
$R^2$ is selected from the group consisting of (a) 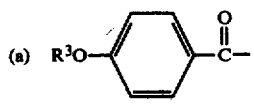

(b) 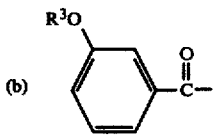

and (c) 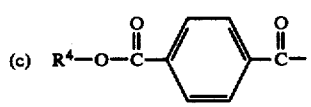

in which formulas
R$^3$ is selected from the group consisting of (a) H;

(b) 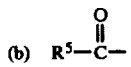

wherein R$^5$ is a straight or branched alkyl group containing 1–4 carbon atoms;
and (c) 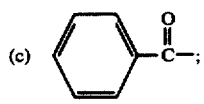;

and wherein
R$^4$ is selected from the group consisting of
(a) H
(b) an alkyl group containing 1–3 carbon atoms.

The formula I thus encompasses mono esters, that is compounds having one hydroxy substituent in position 3 or 5 on the phenyl radical esterified and the other hydroxy substituent unesterified, and diesters, that is compounds having both of the hydroxy groups in the base structure esterified.

Illustrative examples of the radicals R$^1$ and R$^2$ are:

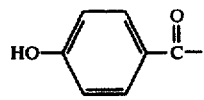

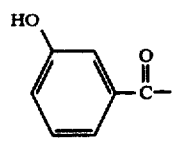

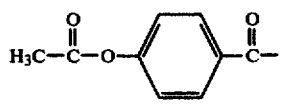

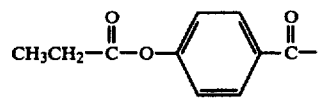

-continued

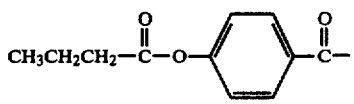

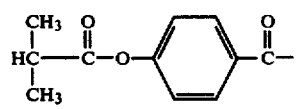

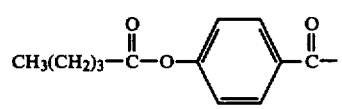

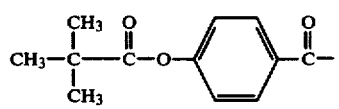

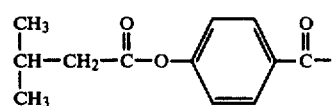

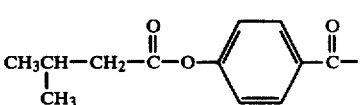

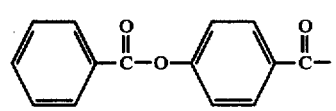

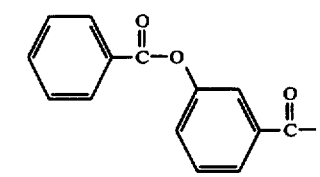

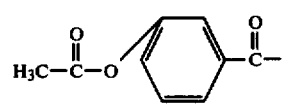

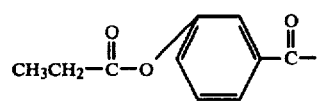

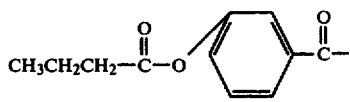

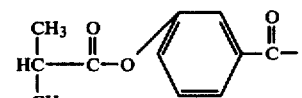

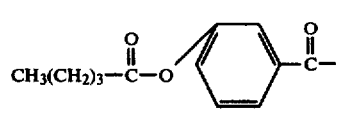

-continued
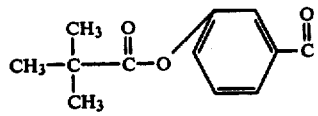
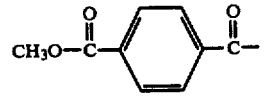
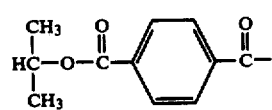
Illustrative examples of compounds of the invention are:
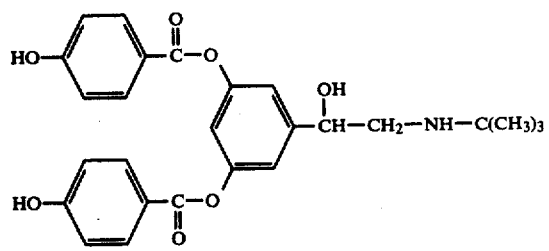
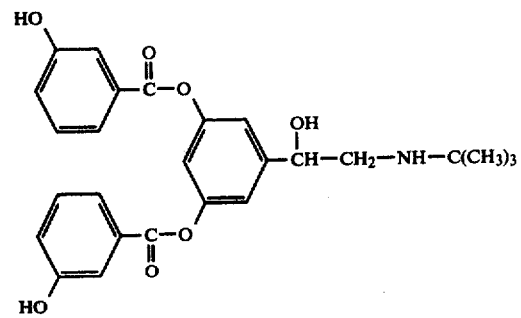
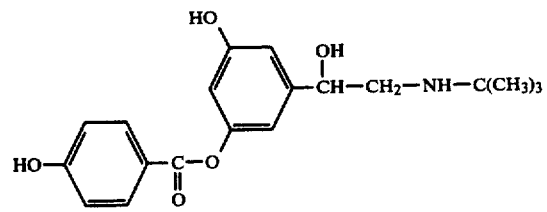
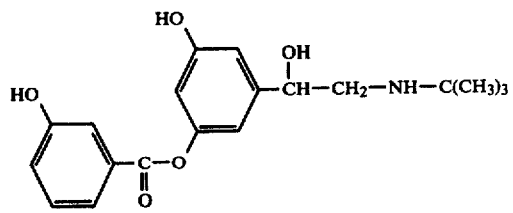

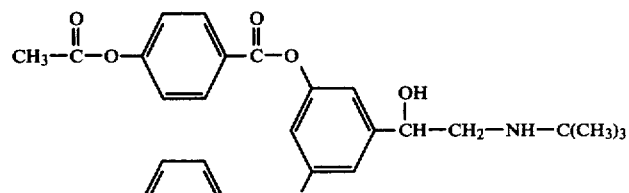
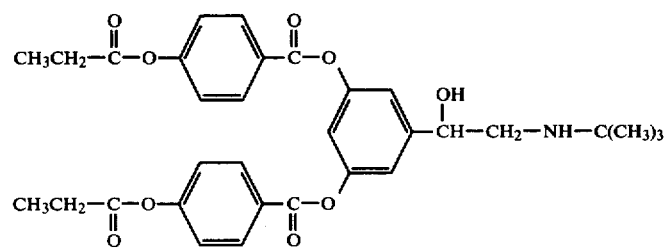
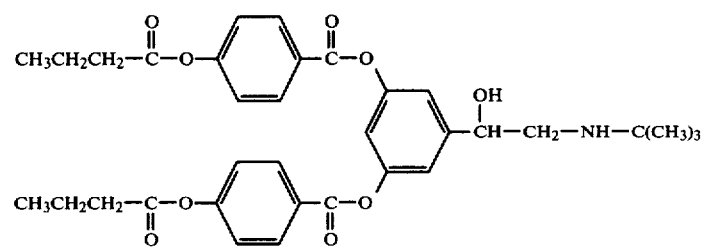
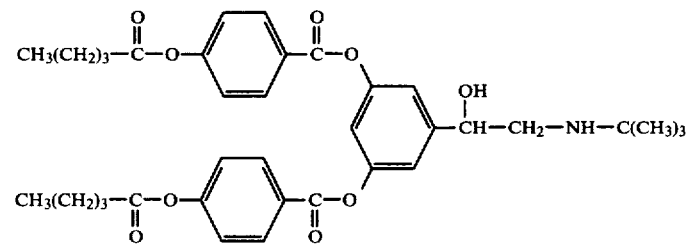
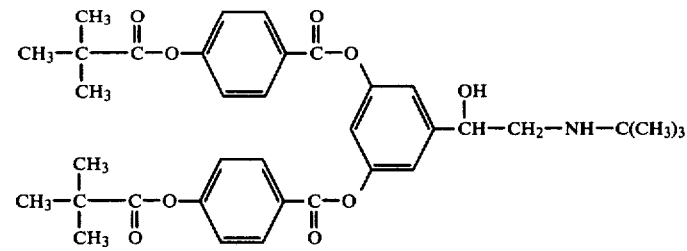
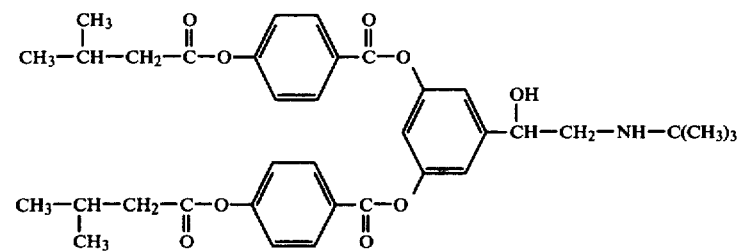

-continued
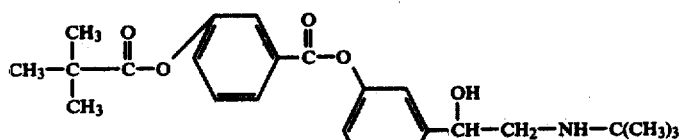
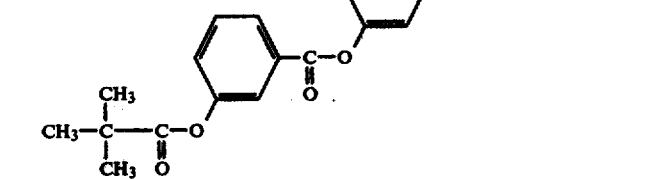
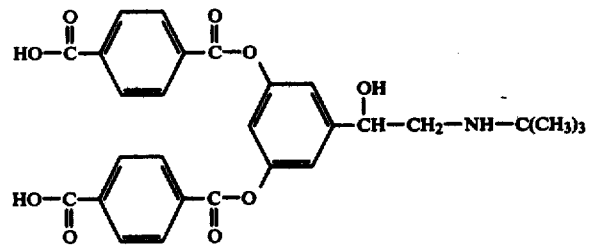
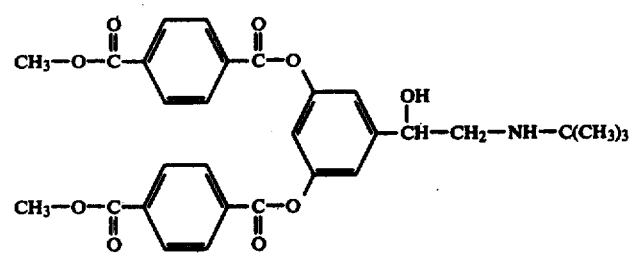
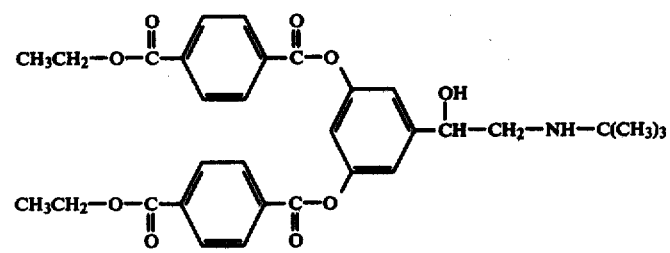
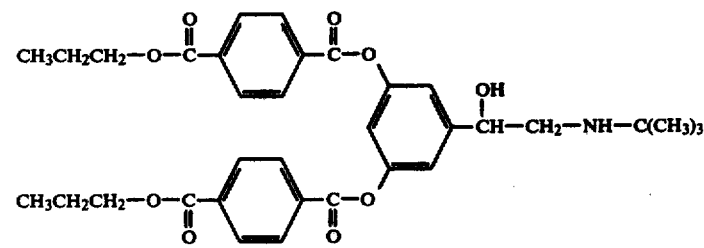

-continued
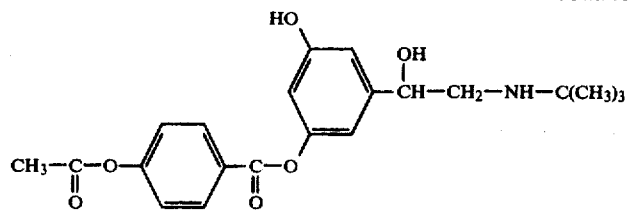
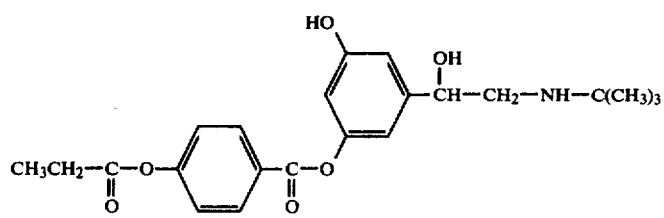
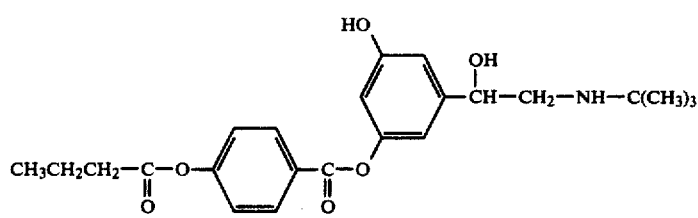
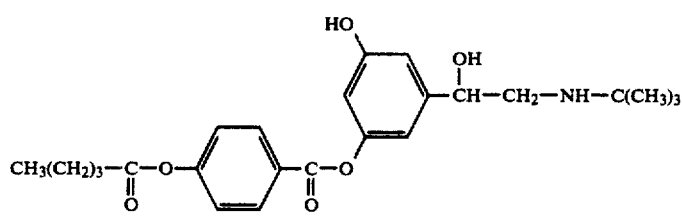
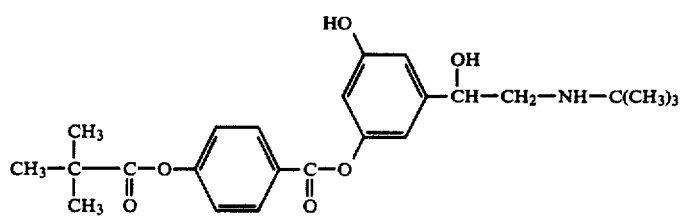
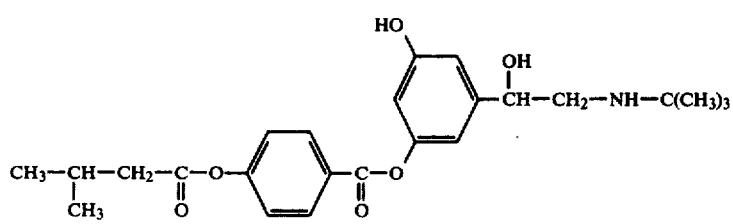
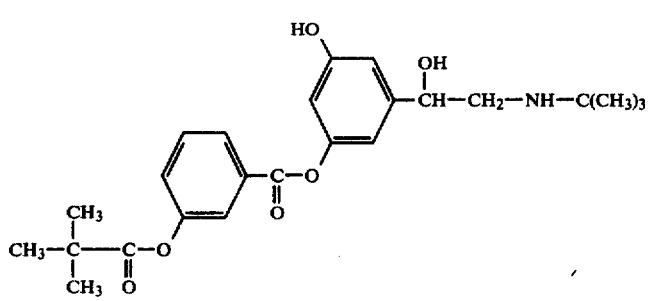

-continued
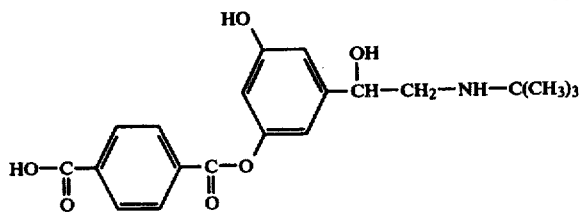
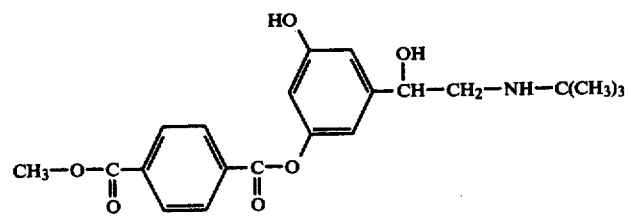
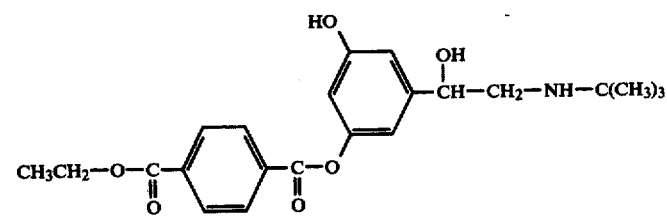
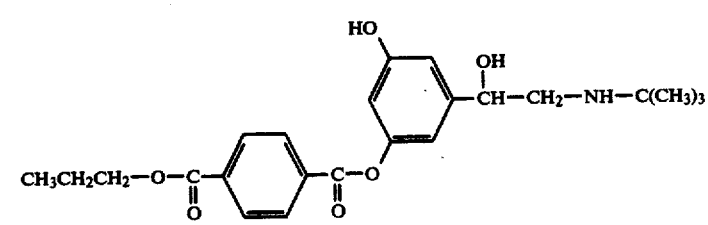
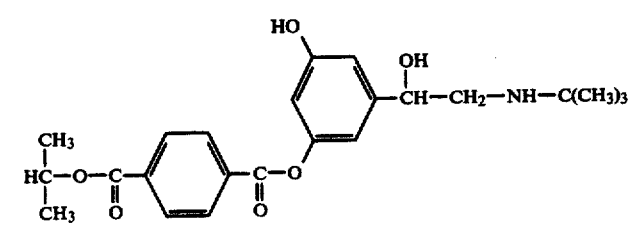
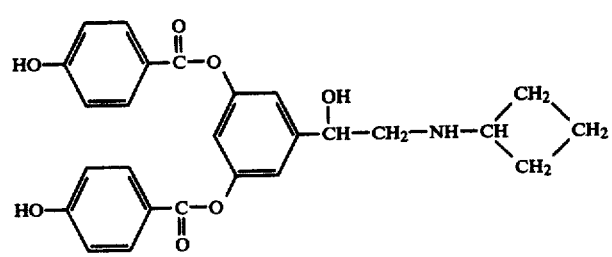
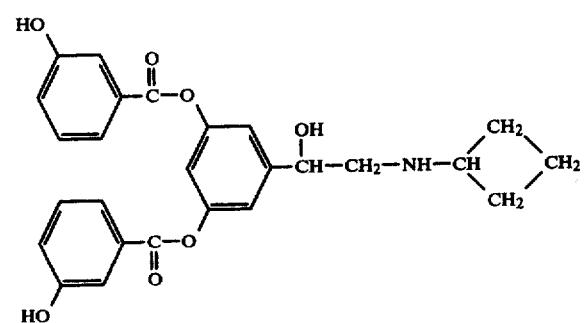

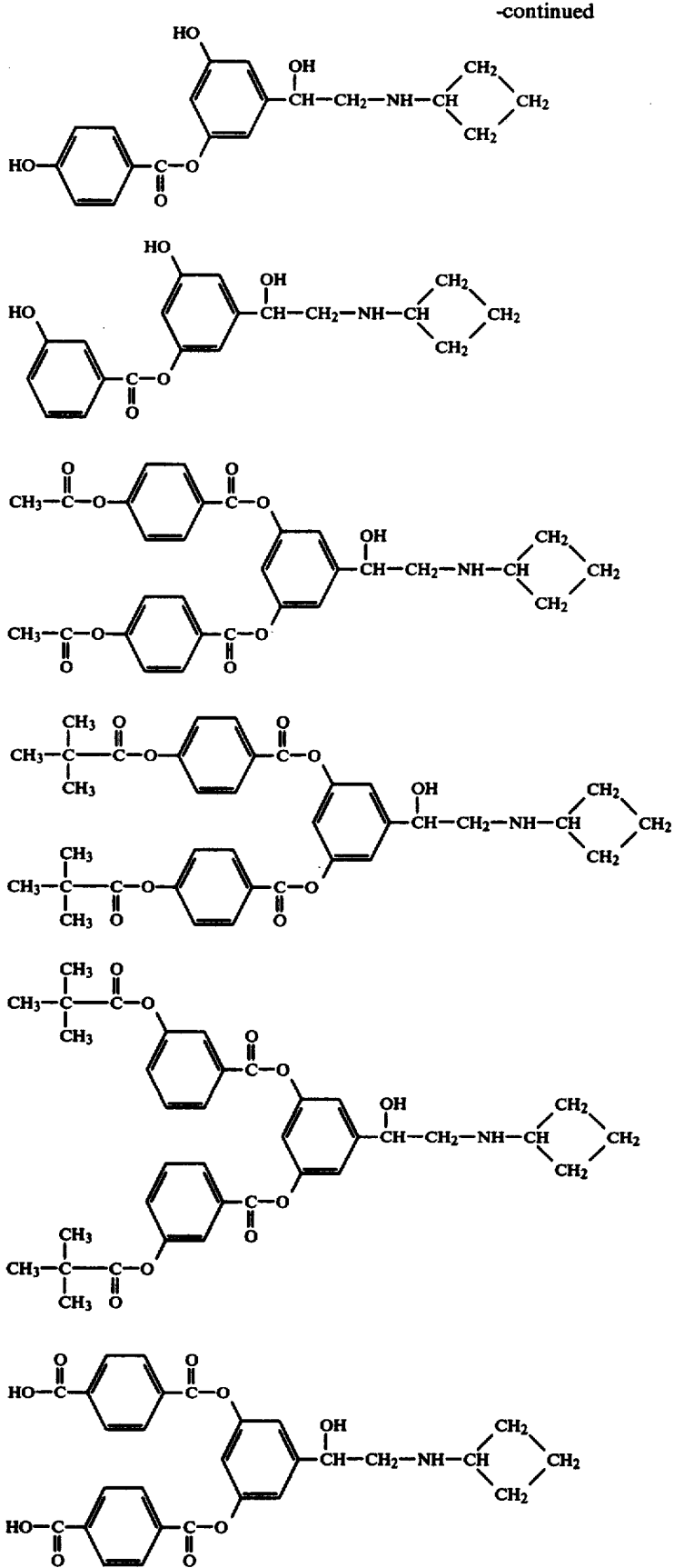

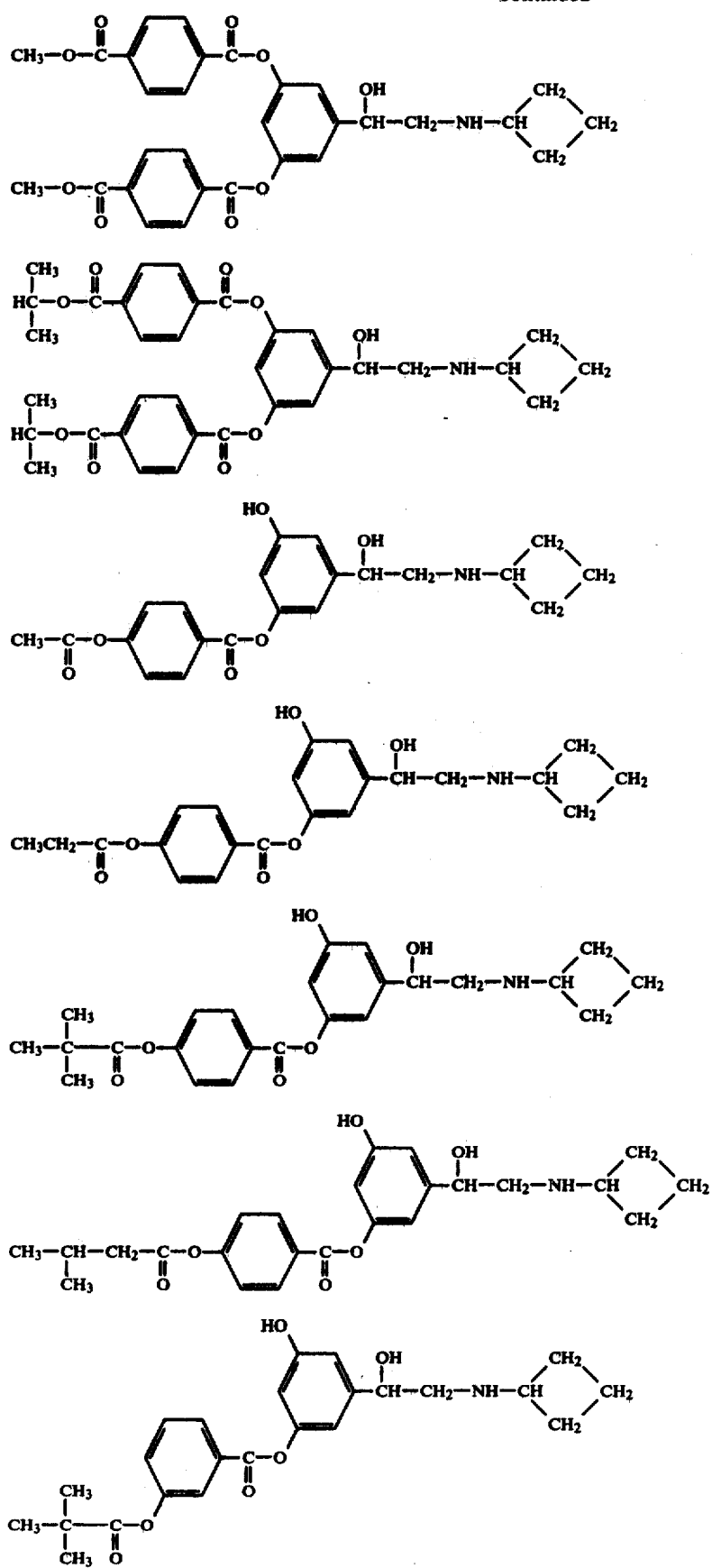

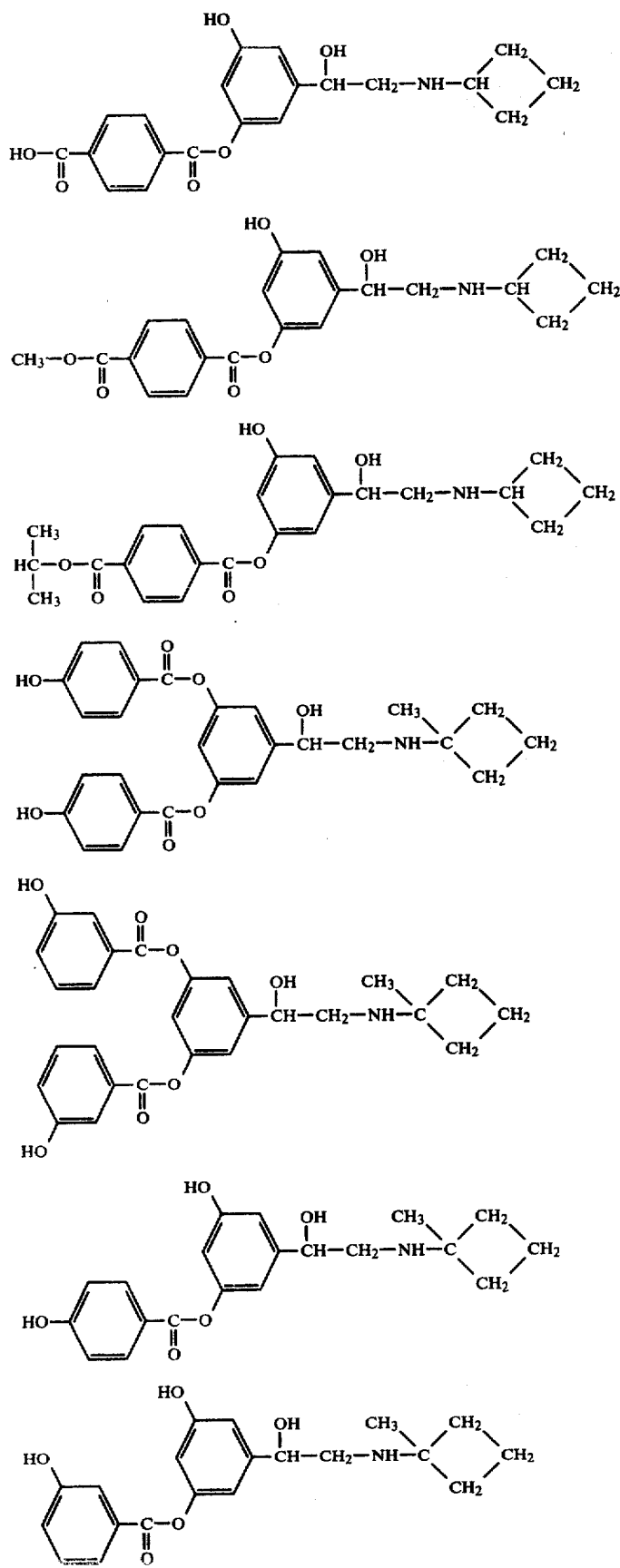

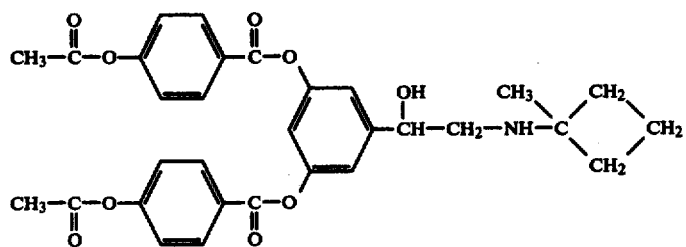
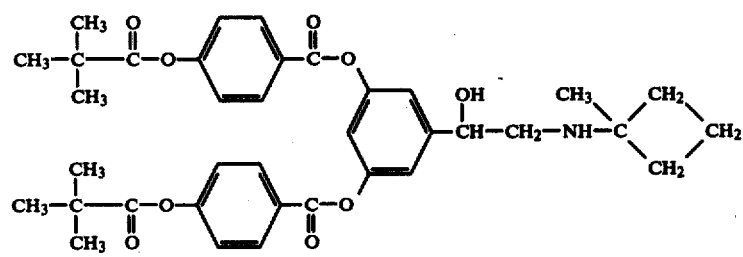
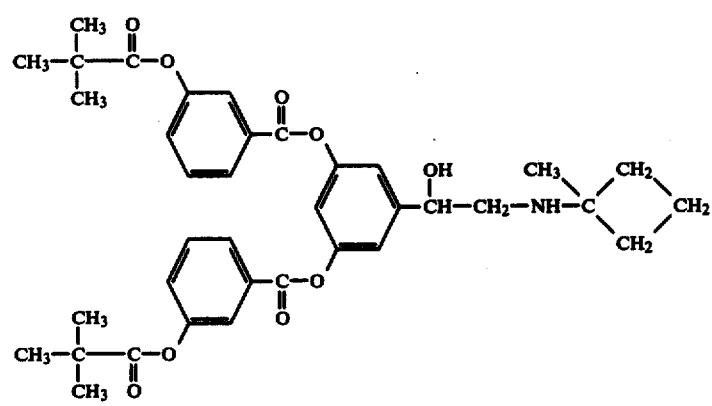
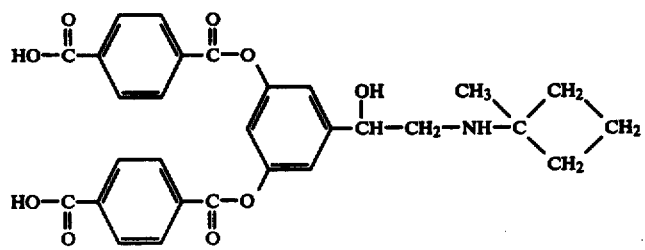
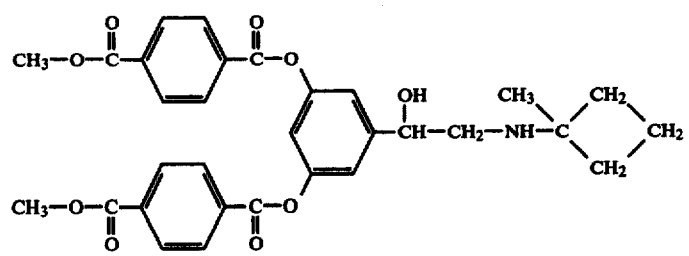

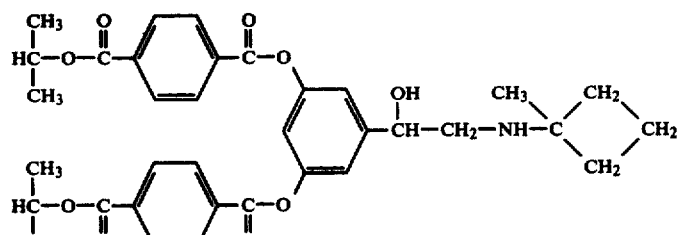
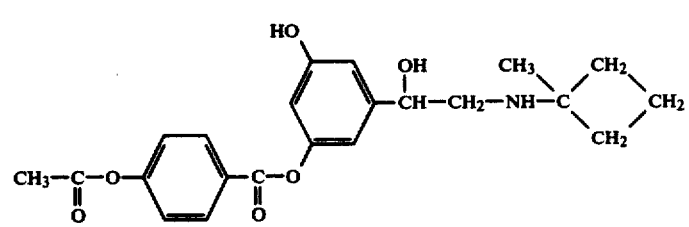
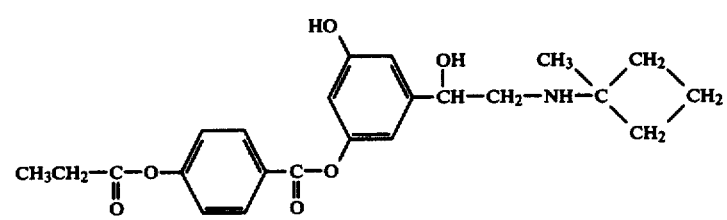
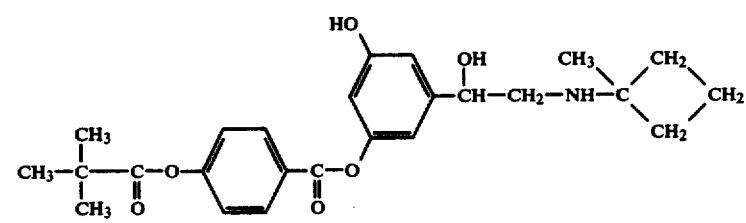
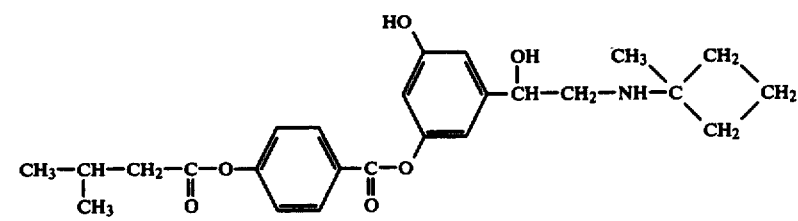
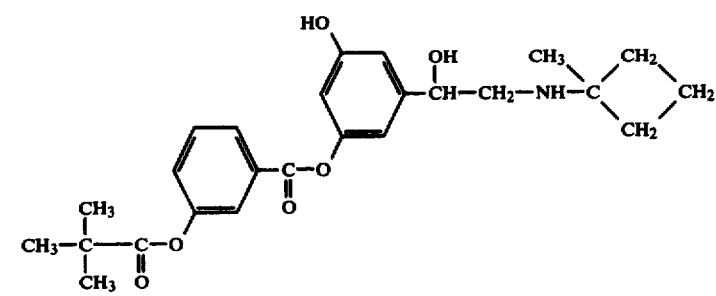
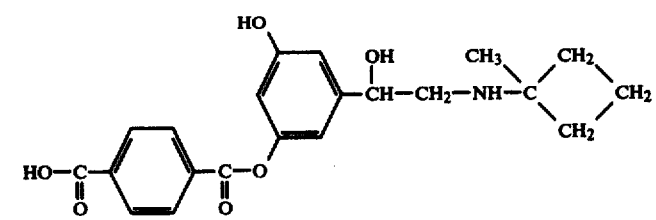

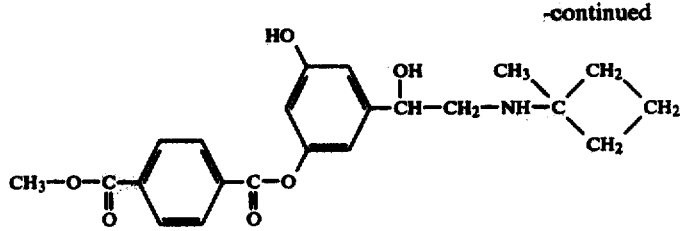

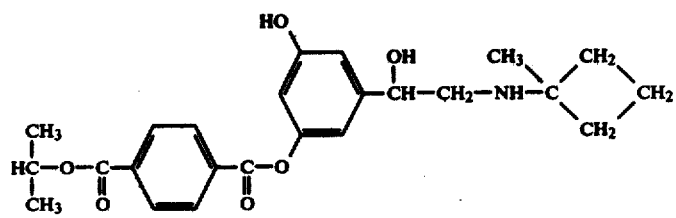

Preferred groups of compounds of the formula I are:
1. Compounds wherein R is —C(CH₃)₃.
2. Compounds of the formula

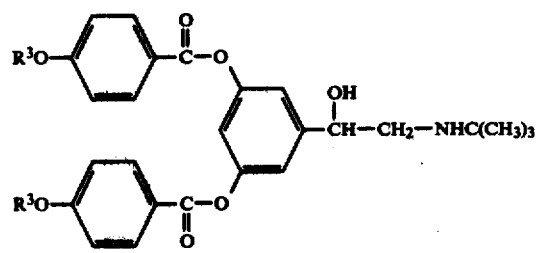

where R³ is as defined previously.
3. Compounds of the formula

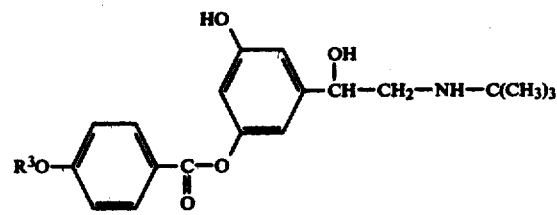

where R³ is as defined previously.
4. Compounds of the formula II and III where R³ is a pivaloyl group.

The preferred compound of the invention is the compound of the formula $$\text{IV}$$

As the compounds of the invention of the formula I possess at least one asymmetric carbon atom, the invention includes all the possible optically active forms and racemic mixtures of the compounds. The racemic mixture may be resolved by conventional methods, for example by salt formation with an optically active acid, followed by fractional crystallisation.

The invention also includes solvates of the compounds of the formula I such as solvates with water—½, 1 or 2 moles of water per mole compound I—and with aliphatic alcohols, 1 mole of the alcohol per mole compound I.

In clinical practice the compounds will normally be administered orally, by injection or by inhalation in the form of a pharmaceutical preparation comprising the active ingredient in the form of the original compound or optionally in the form of pharmaceutically acceptable salt thereof, in association with a pharmaceutically acceptable carrier which may be a solid, semisolid or liquid diluent or an ingestible capsule, and such preparations comprise a further aspect of the invention. The compounds may also be used without carrier material.

As examples of pharmaceutical preparations may be mentioned tablets, drops, aerosol for inhalation, etc. Usually the active substance will comprise between 0.05 and 99, or between 0.1 and 99% by weight of the preparation, for example between 0.5 and 20% for preparations intended for injection and between 0.1 and 50% for preparations intended for oral administration.

The new compounds according to the invention may be administered in the form of salts with physiologically acceptable acids. Suitable acids which may be used are, for example hydrochloric, hydrobromic, sulphuric, fumaric, citric, tartaric, maleic or succinic acid.

The invention further provides pharmaceutical compositions comprising as active ingredient at least one of the compounds according to the invention in association with a pharmaceutical carrier. Such compositions may be designed for oral, bronchial, rectal or parenteral administration.

To produce pharmaceutical preparations in the form of dosage units for oral application containing a compound of the invention in the form of the free base, or a pharmaceutically acceptable salt thereof, the active ingredient may be mixed with a solid, pulverized carrier, for example, lactose, saccharose, sorbitol, mannitol, a starch such as potato starch, corn starch, maize starch or amylopection, a cellulose derivative or gelatin, and also may include lubricants such as magnesium or calcium stearate or a Carbowax or other polyethylene glycol waxes and compressed to form tablets or centers for dragees. If dragees are required, the centers may be coated, for example, with concentrated sugar solutions which may contain gum arabic, talc and/or titanium dioxide, or alternatively with a lacquer dissolved in easily volatile organic solvents or mixtures of organic solvents. Dyestuffs can be added to these coatings. For the preparation of soft gelatin capsules (pearl-shaped closed capsules) consisting of gelatin and, for example, glycerol, or similar closed capsules, the active substance may be admixed with a Carbowax. Hard gelatin capsules may contain granulates of the active substance with solid, pulverized carriers such as lactose, saccharose, sorbitol, mannitol, starches (for example potato starch, corn starch, or amylopectin), cellulose derivatives or gelatin, and may also include magnesium stearate or stearic acid. Dosage units for rectal application may be in the form of suppositories comprising the active substance in admixture with a Carbowax or other polyethylene glycol waxes. Each dosage unit preferably contains 1 to 50 mg active ingredient.

Liquid preparations for oral application may be in the form of syrups, suspensions or emulsions, for example containing from about 0.1% to 20% by weight of active substance and also, if desired, such adjuvants as stabilizing agents, suspending agents, dispersing agents, flavouring agents and/or sweetening agents.

Liquid preparations for rectal administration may be in the form of aqueous solutions containing from about 0.1% to 2% by weight of active substance and also, if desired, stabilizing agents and/or buffer substances.

For parenteral application by injection the carrier may be a sterile, parenterally acceptable liquid, e.g. pyrogen-free water or an aqueous solution of polyvinylpyrrolidone, or a parenterally acceptable oil, e.g., arachis oil and optionally stabilizing agents and/or buffer substances. Dosage units of the solution may advantageously be enclosed in ampoules, each dosage unit preferably containing from 0.1 to 10 mg of active ingredient.

For administration to the bronchia, the compositions are advantageously in the form of a spray solution or spray suspension. The solution or suspension advantageously contains from 0.1 to 10% by weight of the active ingredient.

The dosage at which the active ingredients are administered may vary within a wide range and will depend on various factors such as for example the individual requirements of each patient. A suitable oral dosage range may be from 5 to 200 mg per day.

For treatment in aerosol form, a suitable dosage unit may contain from 0.1 to 10 mg of the active ingredient. One or two such dosage units may be administered at each treatment.

The pharmaceutical compositions containing the active ingredients may suitably be formulated so that they provide doses within these ranges either as single dosage units or as multiple dosage units.

It is indicated in the test results in Table 1 below that the compounds of the present invention have an onset of beta-2-mediated bronchodilating effect which is slower than the onset of the bronchodilating effect of the reference substance terbutaline. This profile of activity will make the compounds of the invention suitable for use not only by themselves in continuous maintenance therapy, but also in acute therapy in combination with bronchodilating drugs which have a faster onset of effect. As examples of known bronchospasmolytically active compounds which are suitable for use in combination with the compounds of the present invention may be mentioned terbutaline, ibuterol, orciprenaline, salbutamol, epinephrine, isoprenaline, and ephedrine.

These compounds have the following structural formulas:

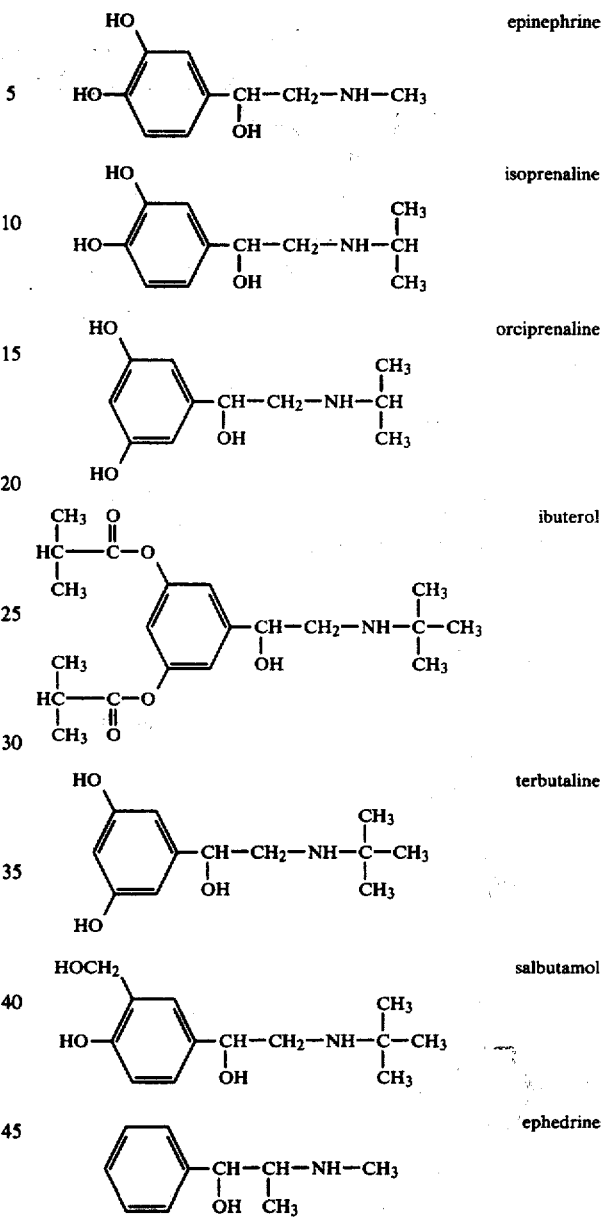

The following bronchospasmolytically active compounds may also be used in combination with the compounds of the invention:

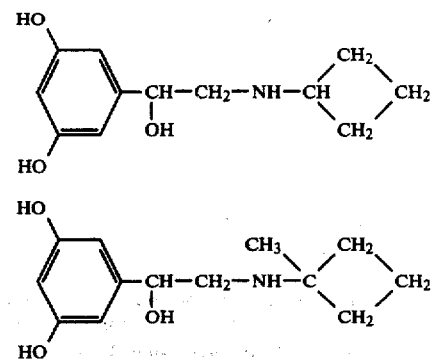

Pharmaceutical combination preparations containing a compound of the invention together with a further bronchospasmolytically active substance with faster onset of effect constitute a further aspect of the present invention.

In pharmaceutical compositions containing a combination of a compound of the formula I with a conventionally used bronchospasmolytic agent such as mentioned above, the weight proportion of the known compound to the compound I of the invention is suitably from 1:2 to 1:5 and, preferably from 1:3 to 1:4.

The compounds of the invention can be prepared by known methods such as (A) Reducing a compound of the formula

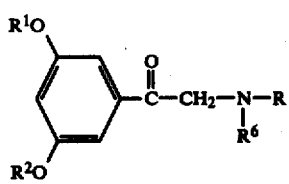　　V wherein R, $R^1$ and $R^2$ are as defined above, and wherein when $R^1$ or $R^2$ is H the resulting hydroxy substituents may be protected by a hydroxy-protecting group, and wherein $R^6$ is hydrogen or a N-protecting group, whereafter, if necessary, remaining protecting groups are replaced by hydrogen.

As examples of groups which can be used for protection of hydroxy substituents in the radicals $R^1$ and $R^2$ can be mentioned ordinarily used hydroxy-protecting groups readily replaceable by hydrogen such as for example alkyl or acyl radicals of not more than 5 carbon atoms or mono- or bicyclic aralkyl groups of not more than 11 carbon atoms such as benzyl or naphthylmethyl.

As examples of groups which can be used for protection of the amino nitrogen atom can be mentioned ordinarily used protecting groups such as mono- or bicyclic aralkyl groups containing not more than 11 carbon atoms such as benzyl and naphthylmethyl.

(B) Reacting a compound of the formula

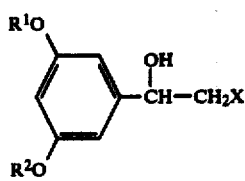　　VI with a compound of the formula

　　VII to the formation of a compound of the formula

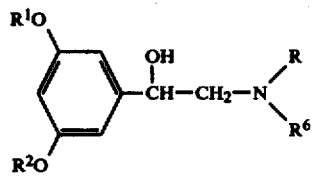　　VIII whereafter, if necessary, protecting groups are replaced by hydrogen, in which formulas R, $R^1$, $R^2$ and $R^6$ are as defined in method A above and wherein X is halogen or a functionally equivalent group capable of reacting with the amine $HNRR^6$ (t-butylamine).

As examples of the radical X can be mentioned groups such as F, Cl, Br, I, or $OSO_2R^7$, wherein $R^7$ is alkyl, aralkyl or aryl.

(C) Reacting a compound of the formula

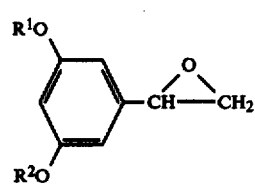　　IX with a compound of the formula

　　VII to the formation of a compound of the formula

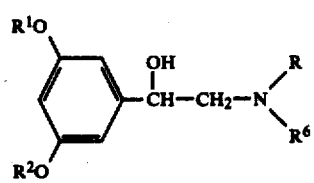　　VIII whereafter, if necessary, protecting groups are replaced by hydrogen, in which formulas R, $R^1$, $R^2$ and $R^6$ are as defined in method a above.

(D) For the preparation of compounds of the formula

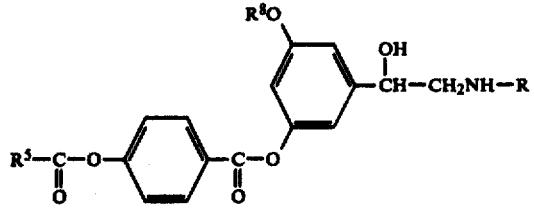　　X wherein $R^5$ is as defined above and $R^8$ is selected from the group consisting of H and the radical

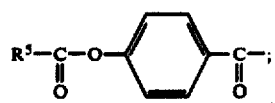

reacting a compound of the formula

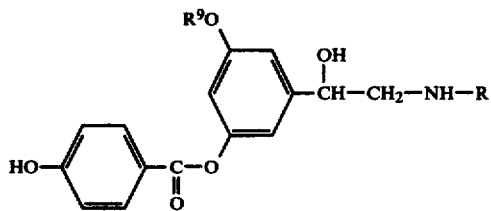   XI with a reactive derivative of the compound of the formula

   XII in which formulas R and $R^5$ are as defined and $R^9$ is a hydroxy-protecting group or the radical

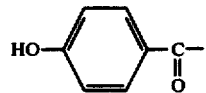

whereafter possible protecting groups are replaced by hydrogen.

As examples of reactive derivatives of the compound of the formula $R^5$—COOH can be mentioned ordinarily used reactive carboxyl groups —CO—Y such as for examples an acid halide such as acid chloride, an alkyl ester, an acid anhydride or a mixed anhydride with formic esters or carboxylic acids, sulphonic or inorganic esters or derivatives obtained by a reaction between a carboxylic acid $R^5$—COOH and a carbodiimide or similarly functioning compounds such as N,N′-carbonyldiimidazole or N-ethyl-5-phenylisoxazolium-3′-sulphonate.

As examples of hydroxy-protecting groups $R^9$ can be mentioned the groups mentioned for that purpose in method A.

(E) For the preparation of compounds of the formula

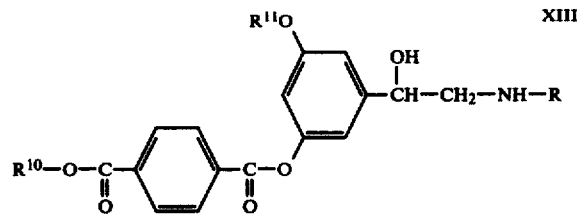   XIII wherein $R^{10}$ is an alkyl group containing 1-3 carbon atoms, and $R^{11}$ is selected from the groups consisting of H and the radical

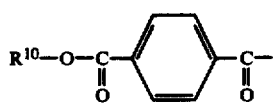

reacting a compound of the formula $R^{10}$—Z   XIV with a compound of the formula

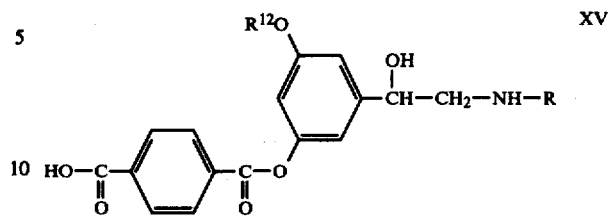   XV wherein R and $R^{10}$ are as defined above; $R^{12}$ is selected from the group consisting of a hydroxy-protecting group and the radical

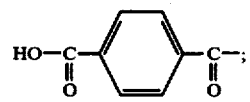

Z is hydroxy or halogen such as Cl or Br;
and wherein the carboxyl radical is an activated carboxyl group;

(F) Reacting a compound of the formula

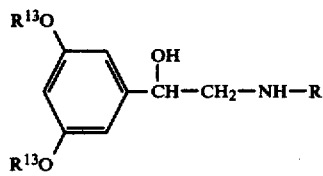   XVI with a compound of the formula $R^2$—OH   XVII wherein the carboxyl group is activated, in which formula R and $R^2$ have the meanings given previously, and wherein $R^{13}$ is H, $R^2$ or a hydroxy-protecting group, provided that at least one radical $R^{13}$ is H and wherein the compound $R^2$—OH is a reactive carboxyl group as illustrated in Method D.

For the preparation of such compounds of the formula I wherein $R^1$ is H, it will be understood that in the methods A-F illustrated above the starting material will be a 3,5-disubstituted compound such as depicted in the methods A-F where the radical —$OR^1$, or corresponding substituent, is a protected hydroxy group, —$OR^{14}$, where the group $R^{14}$ is an ordinary hydroxy protecting group such as exemplified in method A which is replaced by hydrogen in the step where, if necessary, remaining protecting groups are replaced by hydrogen.

Benzyl is a preferred hydroxy-protecting group. Benzyl is also a preferred protecting group for the amino nitrogen.

The compounds of the formula I thus obtained are, if desired, resolved into their optical isomers. The compounds I are also, if desired, converted to pharmaceutically acceptable salts.

The intermediates used in the methods A-F above are in some cases new compounds. It will be illustrated below how the intermediates can be prepared. All reactions illustrated are known. For simplification, the various routes which are possible for preparing the intermediates will be illustrated by specific examples. It will easily be understood how these specific examplifications can be applied for preparing other intermediates which may be required in the preparation of other end compounds. In the formula schemes below, the radical benzyl will be designated Bz.

Routes of preparation for intermediates used in Method A

If in Route A1 an end compound having $R^3 = H$ is to be prepared, the following route may be used:

Route A1:

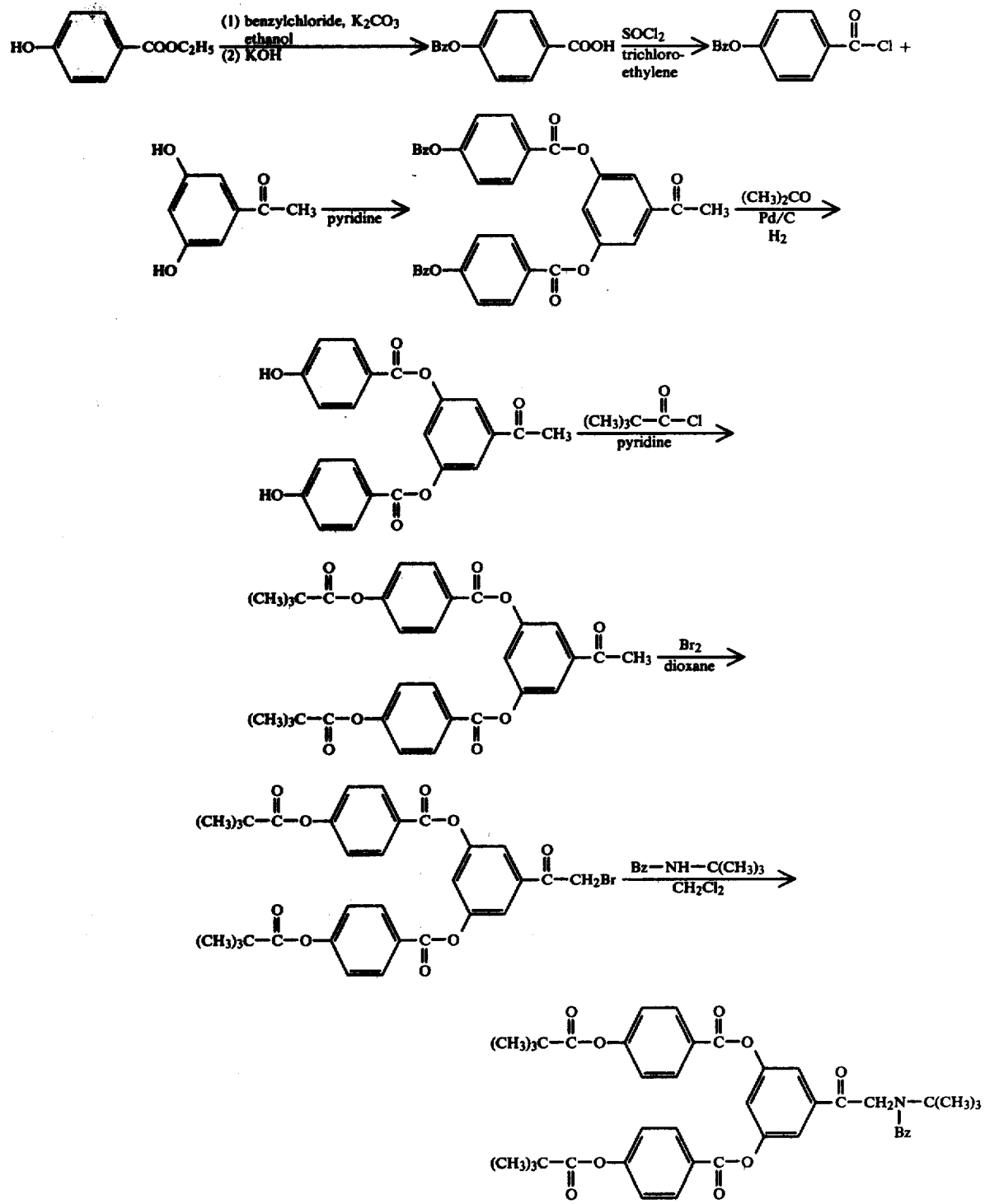

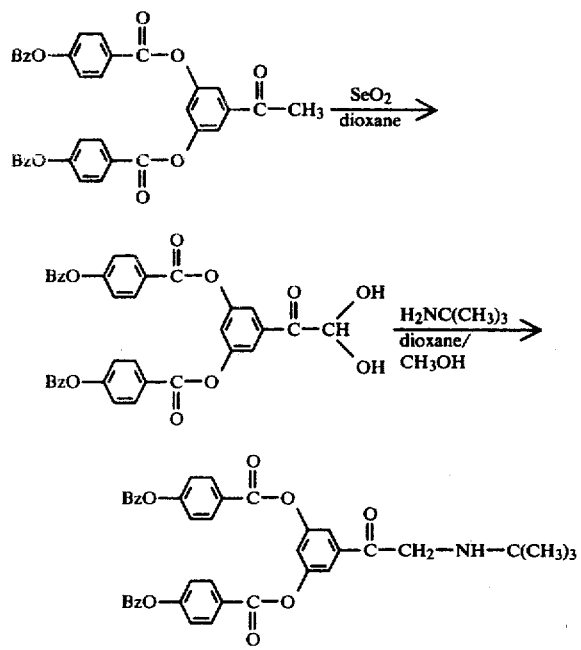

Route A2:

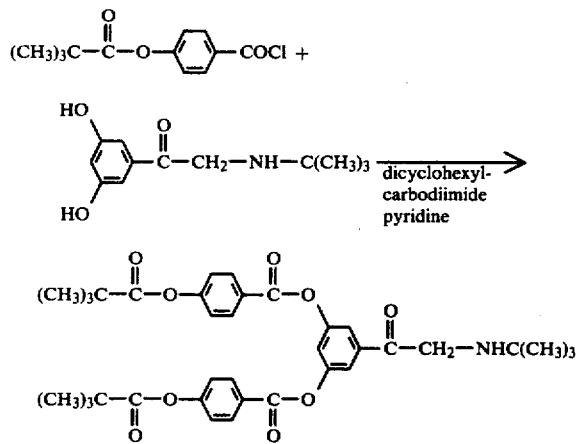

Route of preparation for intermediates used in Method B

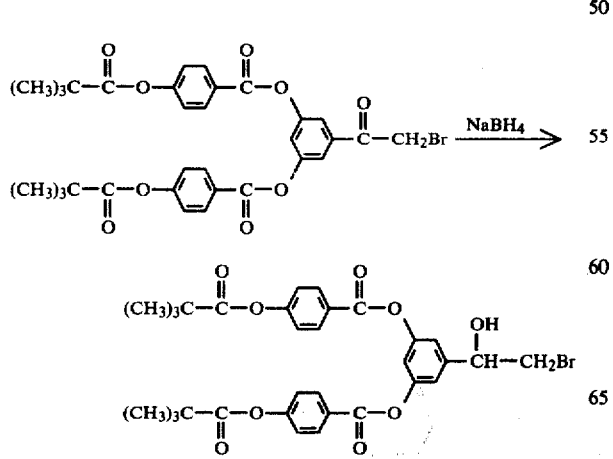

Route of preparation for intermediates used in Method C

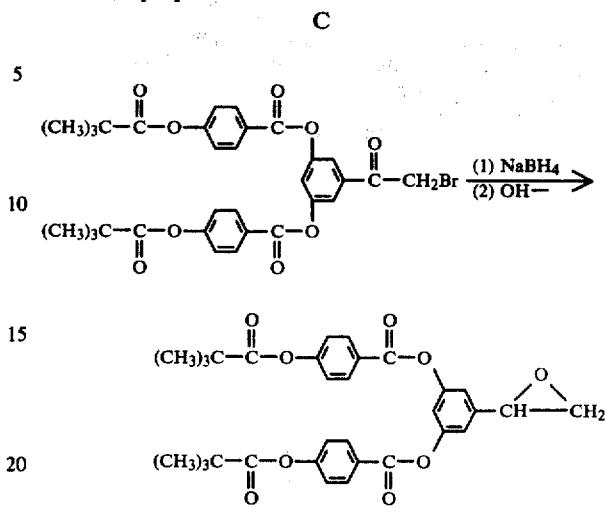

Route of preparation for intermediates used in Methods D, E, and F

The starting material used in these methods is compounds which are per se end compounds of the invention. These starting materials can, therefore, be prepared by routes described in the routes for preparation starting materials in Methods A, B and C. The starting material of the formula

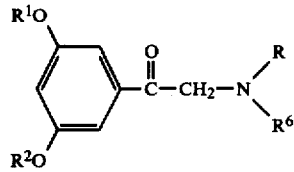

where R, $R^1$, $R^2$ and $R^6$ are as defined in Method A, are novel and constitute as such a further aspect of the invention.

Also the starting material used in Methods D, E and F:

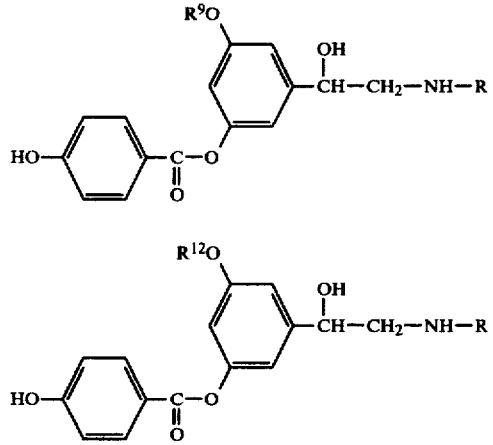

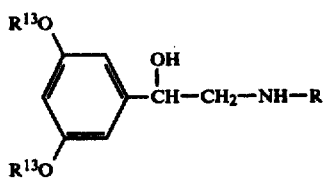

in which formulas R, $R^9$, $R^{12}$ and $R^{13}$ are as defined previously, are novel and constitute an aspect of the invention.

The invention is illustrated by the following examples.

EXAMPLE 1

Preparation of 1-[3,5-bis-(4-pivaloyloxybenzoyloxy)phenyl]-2-t-butylamino ethanol hydrochloride A solution of 118.2 g of 3',5'-bis-(4-pivaloyloxybenzoyloxy)-2-N-benzyl-t-butylamino acetophenone hydrochloride in 1000 ml of $C_2H_5OH$ was hydrogenated at 345 kPa (50 psig) for 4 days in the presence of 3 g of 20% Pd/C, and 1 ml of benzyl chloride. The catalyst was filtered off, and the crystalline residue obtained after evaporation was recrystallized from diethyl ether. The identity of the title compound obtained was confirmed with NMR.

Yield: 35.3 g (33%)
$Cl^-_{calc}$=5.3% $Cl^-_{found}$=5.4%
HPLC: 99.5%
NMR δppm: 1.4 18H (s); 1.5 9H (s); 3.2 2H (m); 5.6 1H (m); 7.7 11H (m). (CDCl3, TMS)

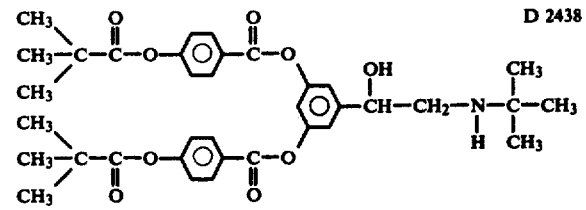

The 3',5'-bis-(4-pivaloyloxybenzoyloxy)-2-N-benzyl-t-butyl-amino acetophenone hydrochloride which was used as starting material was prepared as follows.

(a) 3,5-Bis-(4-pivaloyloxybenzoyloxy)-acetophenone

To a solution of 27.4 g of 3,5-bis-(4-hydroxybenzoyloxy)-acetophenone in 400 ml of pyridine was added 25 ml of pivaloyl chloride. The mixture was stirred for 18 hrs at ambient temperature. The residue after evaporation was dissolved in diethyl ether and washed with hydrochloric acid (pH 3). The ether phase was dried over $MgSO_4$ and evaporated to yield an oil which crystallized from ethanol/ligroin (1:5).

The identity of the product was confirmed with NMR.

Yield: 32 g (82%)
NMR δppm: 1.4 18H (s); 2.6 3H (s); 7.8 11H (m). (CDCl3, TMS)

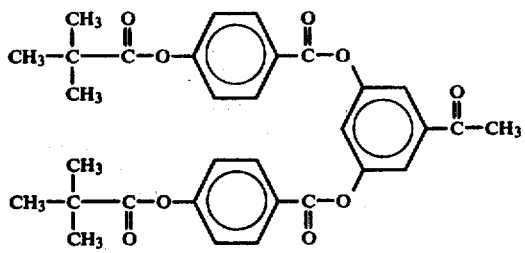

(1b) 3',5'-Bis-(4-pivaloyloxybenzoyloxy)-2-bromo-acetophenone

To a solution of 91.4 g of the acetophenone obtained in step (a) in 800 ml of dioxane was added 8.7 ml of bromine in 200 ml of dioxane. The mixture was stirred at ambient temperature for 2 hrs. The residue obtained after evaporation was dissolved in diethyl ether, treated with activated carbon, filtered, and evaporated. The residue was recrystallized from $C_2H_5OH$. The identity of the product was confirmed with NMR.

NMR δppm: 1.4 18H (s); 4.4 2H (s); 7.7 11H (m). (CDCl3, TMS)

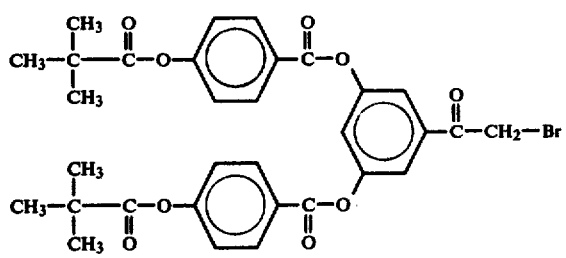

(1c) 3',5'-Bis-(4-pivaloyloxybenzoyloxy)-2-N-benzyl-t-butylamino acetophenone hydrochloride To a solution of 73.6 g of the bromoketone obtained in step (b) in 900 ml of acetone was added 40.8 g of N-benzyl-t-butylamine in 100 ml of acetone. The mixture was refluxed under stirring for 24 hrs. The residue obtained after evaporation was dissolved in diethyl ether. The precipitated N-benzyl-t-butylamino hydrobromide was filtered off (25.1 g). To the filtrate was added 125 ml of 2 N HCl in 100 ml of water. The crystalline precipitate formed was filtered off and washed with water and diethyl ether. The identity of the product was confirmed with NMR. Yield: 51.1 g (59%)

NMR δppm: 1.4 18H (s); 1.7 9H (s); 4.8 4H (m); 7.7 16H (m). (CDCl3, TMS)

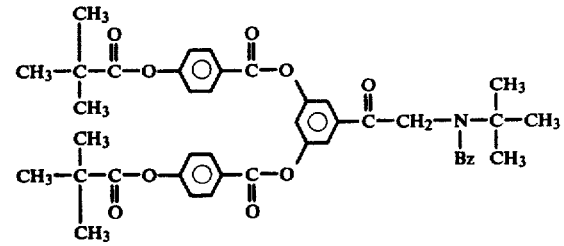

EXAMPLE 2

Preparation of
1-[3,5-bis-(4-isobutyryloxybenzoyloxy)phenyl]-2-t-butylamino ethanol hydrochloride A solution of 100 g of 3',5'-bis-(4-isobutyryloxybenzoyloxy)-2-N-benzyl-t-butylamino acetophenone hydrochloride in 600 ml of ethanol was hydrogenated in the presence of 3 g of 10% Pd/C in a Parr pressure apparatus for 24 hrs at ambient temperature and 345 kPa (50 psig). The catalyst was filtered off and the filtrate evaporated to yield a yellow oil which crystallized from isopropylalcohol/diethylether.

This product was dissolved in 700 ml of ethanol, 1 ml of benzyl chloride plus 2 g of 20% Pd/C was added, and the mixture was hydrogenated at 345 kPa (50 psig) and ambient temperature for another 24 hrs. The mixture was worked up in the same manner as described above. The product was recrystallized from isopropylalcohol. The identity of the title product obtained was confirmed with NMR.

Yield: 26.4 g
HPLC: 98%

NMR δppm: 0.85 9H (s); 1.0 12H (d); 1.6 CD$_3$COCD$_3$; 2.45 2H (m); 2.8 2H (m); 5.15 1H (d); 5.9 1H (broad); 7.35 11H (m). (CD$_3$COCD$_3$, TMS)

Cl$^-$$_{calc}$: 5.5% Cl$^-$$_{found}$: 5.5%

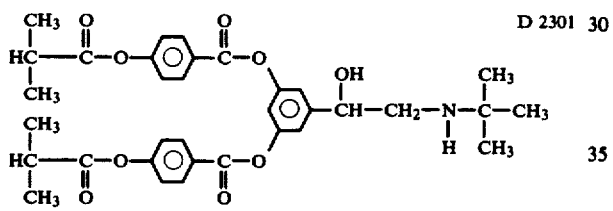

The 3',5'-bis-(4-isobutyryloxybenzoyloxy)-2-N-benzyl-t-butylamino acetophenone hydrochloride which was used as starting material was prepared as follows.

(2a) 3,5-Bis-(4-isobutyryloxybenzoyloxy)-acetophenone

To a solution of 44.8 g 3,5-bis-(4-hydroxybenzoyloxy)acetophenone in 500 ml of pyridine was added 28 ml of isobutyric acid chloride. The mixture was stirred at ambient temperature for 18 hrs. The residue after evaporation was taken up in diethyl ether/H$_2$O. The diethyl ether phase was washed with 2 N HCl and then water. The combined ether phase were dried over MgSO$_4$, treated with activated charcoal, filtered, and evaporated. The residual oil was crystallized from ethanol. The identity of the product was confirmed with NMR.

Yield: 44.0 g (75%)

NMR δppm: 1.15 12H (d); 2.6 3H (s); 2.8 2H (m); 7.7 11H (m). (CDCL$_3$, TMS)

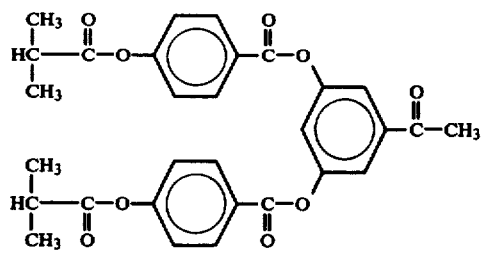

(2b) 3',5'-Bis-(4-isobutyryloxybenzoyloxy)-2-bromoacetophenone

To a solution of 44 g of the acetophenone obtained in step (a), dissolved in 400 ml of dioxane was added dropwise under stirring a solution of 4.6 ml bromine in 100 ml of dioxane. The mixture was stirred at ambient temperature for 2 hrs.

After evaporation, the residue was dissolved in diethyl ether and treated with activated charcoal. The filtrate was evaporated and the residue recrystallized from ethanol. The identity of the product was confirmed with NMR.

Yield: 43.9 g (86%)

NMR δppm: 1.15 12H (d); 2.8 2H(m); 4.4 2H (s); 7.75 11H (m). (CDCl$_3$, TMS)

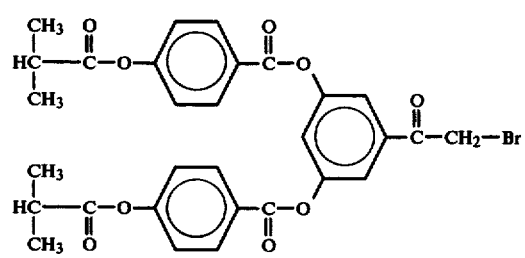

(2c) 3',5'-Bis-(4-isobutyryloxybenzoyloxy)-2-N-benzyl-t-butylamino-acetophenone hydrochloride To a solution of 56 g of the bromoketone obtained in step (b) in 500 ml CH$_2$Cl$_2$ was added 32.7 g benzyl-t-butylamine. The mixture was stirred under reflux for 48 hrs. The residue after evaporation was dissolved in diethyl ether. The precipitated benzyl-t-butylamine hydrobromide (21 g) was filtered off. The filtrate was chilled (+5° C.) and 100 ml of 2 N HCl was added under stirring. The precipitated crystals were filtered off and washed with water and diethyl ether. The identity of the product was confirmed with NMR.

Yield: 40.7 g (62%)

NMR ppm: 1.35 12H (d); 1.75 9H (s); 2.85 2H (m); 4.75 4H (m); 7.8 16H (m). (CDCl$_3$, TMS)

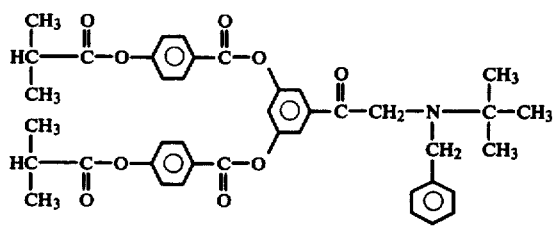

EXAMPLE 3

Preparation of
1-(3,5-bis-[4-benzoyloxybenzoyloxy]phenyl)-2-t-butylamino ethanol hydrochloride A solution of 1.3 g of 3',5'-bis-(4-benzoyloxybenzoyloxy)-2-N-benzyl-t-butylamino acetophenone hydrochloride in 75 ml of ethanol was hy;rogenated at 345 kPa (50 psig) for 18 hrs at ambient temperature in the presence of 0.3 g 10% Pd/C. The catalyst was filtered off and the filtrate evaporated. The residue crystallized from ethanol/diethyl ether and was then recrystallized from ethanol. The identity of the title product obtained was confirmed with NMR.

Yield: 0.5 g $Cl^-_{calc} = 5.0\%$ $Cl^-_{found} = 4.9\%$

NMR δppm: 0.85 9H (s); 1.95 DMSO-d₆; 2.9 2H (m); 4.2 1H (m, broad); 7.4 21H (m). (DMSO-d₆, TMS)

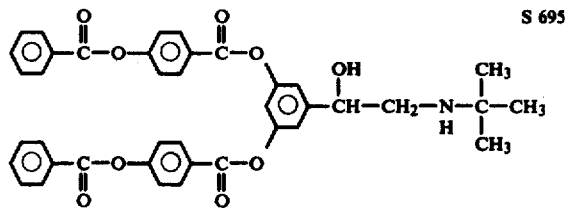

S 6955

The 3',5'-bis-(4-benzyloxybenzoyloxy)-2-N-benzyl-t-butylamino acetophenone hydrochloride which was used as starting material was prepared as follows.

(3a) 4-Benzyloxybenzoic acid

A mixture of 132.5 g ethyl-4-hydroxybenzoate, 135 g $K_2CO_3$ and 110 ml benzyl chloride in 900 ml of ethanol was refluxed under stirring for 18 hrs. The mixture was warm filtered, and the filtrate evaporated. The residue was dissolved in 700 ml of water, 98 g of KOH was added, whereafter the mixture was refluxed with stirring for 2 hrs, or until a clear solution was obtained. The pH of the solution was adjusted to pH 1 with conc. HCl, and the crystalline material formed was filtered off. The identity of the product was confirmed with NMR.

Yield: 162.4 g (89%)

NMR δppm: DMSO-d₆ 2.4; 5.1 2H (s); 7.4 9H (m) (DMSO-d₆, TMS)

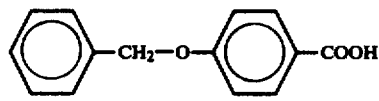

(3b) 4-Benzyloxybenzoyl chloride

A solution of 164.7 g 4-benzyloxybenzoic acid obtained in step (a) and 80 ml of thionyl chloride in 750 ml of trichloroethylene was refluxed with stirring for 3 hrs. The crystalline residue obtained after evaporation was recrystallized from petroleum ether b.p. 80°–110° C.

The identity of the product was confirmed with NMR.

Yield: 165.8 g (93%)

NMR δppm: 5.2 2H (s); 7.6 9H (m) (CDCl₃, TMS)

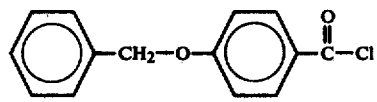

(3c) 3,5-Bis-(4-benzyloxybenzoyloxy)-acetophenone

To a solution of 50 g of 3,5-dihydroxy acetophenone obtained in step (b) in 500 ml of pyridine was added 198.9 g of 4-benzyloxybenzoyl chloride.

The mixture was stirred at ambient temperature for 18 hrs. After evaporation, the residue was partitioned between methylene chloride and water. The CH₂Cl₂- phase was evaporated, and the residue recrystallized once from methanol, and once from ethyl acetate/methanol. The identity of the product was confirmed with NMR.

Yield: 151 g (80%)

NMR δppm: 2.6 3H (s); 5.2 4H (s); 7.7 21H (m) (CDCl₃, TMS)

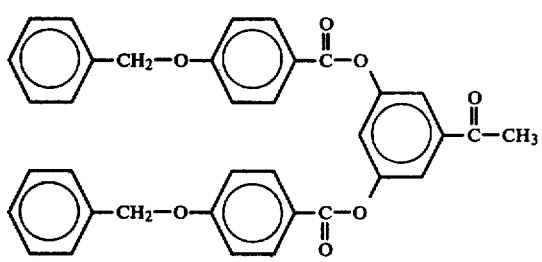

(3d) 3,5-Bis-(4-hydroxybenzoyloxy)-acetophenone

A slurry of 143.8 g of 3,5-bis-(4-benzyloxy-benzoyloxy)-acetophenone obtained in step (c) in 1000 ml of acetone was heated to 45° C., and hydrogenated in the presence of 3 g 10% Pd/C at atmospheric pressure for 6 hrs when the calculated amount hydrogen (11.3 l) had been consumed.

The crystalline residue obtained after evaporation was recrystallized from isopropylalcohol/petroleum ether. The identity of the product was confirmed with NMR.

Yield: 90.5 g (92%)

NMR δppm: DMSO-d₆ 2.4; 2.5 3H (s); 7.5 11H (m) (DMSO-d₆, TMS)

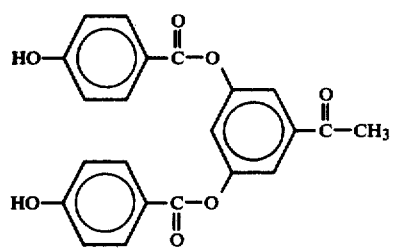

(3e) 3,5-Bis-(4-benzoyloxybenzoyloxy)-acetophenone

To a solution of 11.8 g of 3,5-bis-(4-hydroxyben-zoyloxy)-acetophenone obtained in step (d) in 200 ml of pyridine was added 10.5 ml of benzoyl chloride. The mixture was stirred at 70° C. for 18 hrs. The residue after evaporation was partitioned between H₂O/CHCl₃. The CHCl₃-phase was washed with 2 N HCl and water, and then dried over MgSO₄. The crystals obtained after evaporation was refluxed in EtOH, and then filtered. The identity of the product was confirmed with NMR.

Yield: 18.0 g

NMR δppm: 1.19 3H (s); 7.1 21H (m). (CDCl₃, TMS)

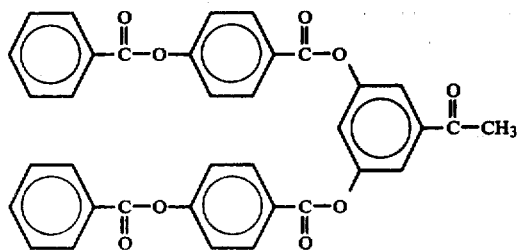

(3f)
3',5'-Bis-(4-benzoyloxybenzoyloxy)-2-bromo-acetophenone

To a solution of 9 g of the acetophenone obtained in step (e) in 200 ml of warm dioxane was added a solution of 0.9 ml bromine in 30 ml of dioxane. The mixture was stirred at ambient temperature for 2 hrs. The crystalline residue obtained after evaporation was boiled with ethanol. The identity of the product was confirmed with NMR.

Yield: 10.1 g (99%)
NMR δppm: 3.65 2H (s); 7.05 21H (m). (CDCl$_3$, TMS)

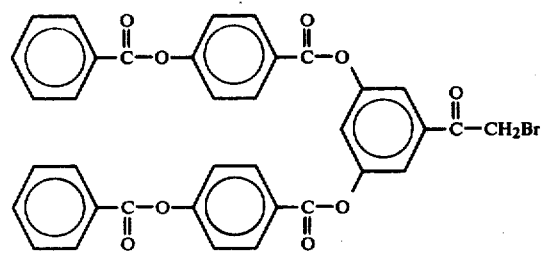

(3g)
3',5'-Bis-(4-benzoyloxybenzoyloxy)-2-N-benzyl-t-butylamino acetophenone hydrochloride To a solution of 5.1 g of the bromoketone obtained in step (f) in 100 ml of CH$_2$Cl$_2$ was added a solution of 2.45 g of N-benzyl-t-butylamine in 25 ml of CH$_2$Cl$_2$. The mixture was refluxed with stirring for 18 hrs. After evaporation, the residue was taken up in diethyl ether. The ether was decanted to which then 2 N HCl was added with stirring. The crystalline precipitate formed was filtered off and washed with water and diethyl ether. Recrystallization was performed from ethanol/diethyl ether. The identity of the product was confirmed with NMR.

Yield: 1.4 g
NMR δppm: 1.0 9H (s); 2.9 4H (m, broad); 7.0 26H (m). (CDCl$_3$, TMS)

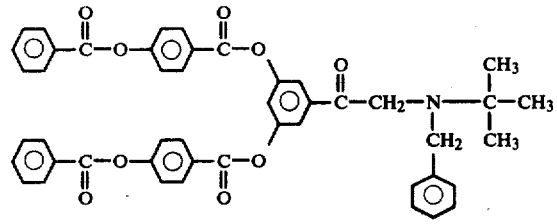

EXAMPLE 4
Preparation of 1-[3,5-bis-(4-hydroxybenzoyloxy)phenyl]-2-t-butylamino ethanol sulphate (4a)
1-[3,5-bis-(4-benzyloxybenzoyloxy)phenyl]-2-t-butylamino ethanol sulphate To a solution of 8.2 g of 3,5-bis-(4-benzyloxybenzoyloxy)-phenyl glyoxal in 80 ml of dioxane, and 160 ml of methanol was added 1.5 g of t-butylamine. The mixture was stirred at ambient temperature for 18 hrs, whereafter 0.04 moles of NaBH$_4$ was added. After stirring for 2 hrs the mixture was evaporated, and the residue partitioned between ether and water. The ether phase was dried over MgSO$_4$ and evaporated. The residue was dissolved in ethanol, and sulphuric acid added until pH was 5.5. A crystalline precipitate was formed.

Yield: 3.0 g
SO$_4{}^{2-}$ found: 98.5%

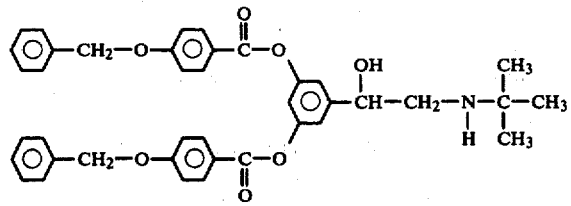

(4b)
1-[3,5-bis-[4-hydroxybenzoyloxy)phenyl]-2-butylamino ethanol sulphate

A solution of 2.8 g of 1-[3,5-bis-(4-benzyloxybenzoyloxy)-phenyl]-2-t-butylamino ethanol sulphate obtained in step (a) above in 150 ml of methanol was hydrogenated in the presence of 0.5 g of 10% Pd/C at ambient temperature and a pressure of 345 kPa (50 psig) for 18 hrs. The catalyst was filtered off and the residue recrystallized from isopropylalcohol/diethyl ether. The identity of the title product obtained was confirmed with NMR.

Yield: 0.7 g
NMR δppm: 0.95 9H (s); 2.7 2H (m); 2.9 CD$_3$OD; DOH 4.45; 4.85 1H (m); 6.95 11H (m). (CD$_3$OD)
HPLC: 96.5%
SO$_4{}^{2-}$: 96%

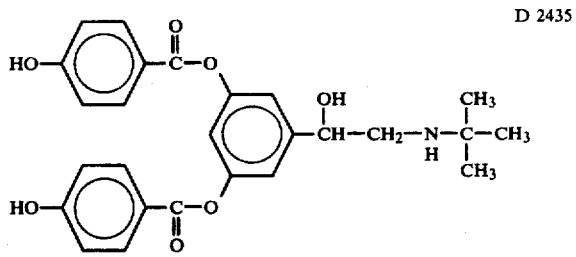

D 2435

The 3,5-bis-(4-benzyloxybenzoyloxy)phenyl glyoxal which was used as starting material was prepared as follows.

3,5-Bis-(4-benzyloxybenzoyloxy)phenyl glyoxal

To a solution of 11.5 g 3,5-bis-(4-benzyloxybenzoyloxy)-acetophenone in 200 ml of dioxane was added 2.7 g of SeO₂ in 10 ml of water. The mixture was refluxed with stirring for 18 hrs. After filtering and evaporation of the filtrate, the residue was partitioned between diethyl ether and water. The light yellow oil obtained after evaporation of the ether phase was crystallized from methanol. The identity of the product was confirmed with NMR.

Yield: 8.2 g

NMR (mono methyl acetal) δppm: 1.8 1H (s); 2.75 3H (s); 4.40 4H (s); 4.8 1H (s); 6.8 21H (m). (CDCl₃, TMS)

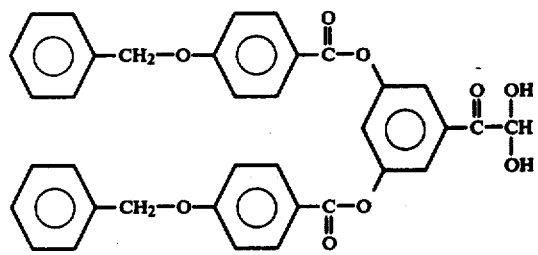

EXAMPLE 5

Preparation of 1-[3,5-bis-(4-pivaloyloxybenzoyloxy)phenyl]-2-t-butylaminoethanol hydrochloride A solution of 3.2 g (0.005 moles) of 1-[3',5'-bis-(4-pivaloyloxybenzoyloxy)phenyl]-2-bromoethanol and 1.1 g (0.015 moles) of t-butylamine in 100 ml of methylene chloride was boiled under reflux for 18 hrs. After evaporation to dryness, diethyl ether was added to the residue. The precipitated t-butylamino hydrobromide (0.2 g) was filtered off and the filtrate was then acidified with ethanolic hydrochloric acid. HPLC analysis of this solution showed the presence of the title compound as compared with an authentic sample.

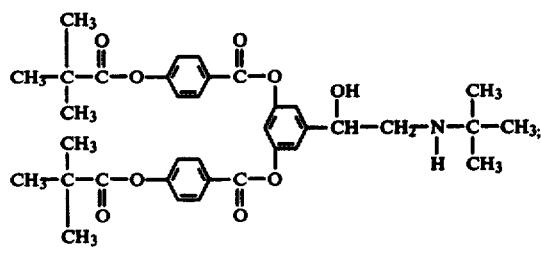

The 1-[3',5'-bis-(4-pivaloyloxybenzoyloxy)phenyl]-2-bromoethanol which was used as starting material was prepared as follows.

1-[3',5'-Bis-(4-pivaloyloxybenzoyloxy)phenyl]-2-bromoethanol

To a solution of 7.8 g (0.012 moles) of 3',5'-bis-(4-pivaloyloxybenzoyloxy)-2-bromoacetophenone in 200 ml of dioxane and 40 ml of water was added portionally 0.45 g (0.012 moles) of NaBH₄ dissolved in 30 ml of water. After each addition pH was adjusted with 1 N HCl so that the pH of the reacting mixture never exceeded pH 7. The mixture was stirred at ambient temperature for 1 h, whereafter the solution was evaporated to dryness and the residue taken up in diethyl ether. The ether phase was washed with water, dried over MgSO₄ and then evaporated to dryness to yield a crystalline residue. The identity of the product was confirmed with NMR.

Yield: 6.7 g (87%)

NMR (CDCl₃) δppm: 1.43 18H (s); 3.70 2H (m); 5.05 1H (m); 7.82 11H (m).

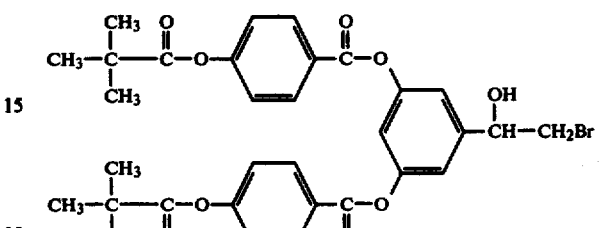

EXAMPLE 6

Preparation of 1-[3,5-bis-(4-pivaloyloxybenzoyloxy)phenyl]-2-cyclobutylaminoethanol sulphate A solution of 2.2 g of 3',5'-bis-(4-pivaloyloxybenzoyloxy)-2-cyclobutylamino acetophenone hydrochloride in 75 ml of ethanol was hydrogenated at 380 kPa (55 psig) and 45° C. for 18 hrs in the presence of 0.4 g 10% Pd/C. After filtering off the catalyst the filtrate was evaporated to dryness to give an oil as residue. This oil was partitioned between ethyl ether and 10% sodium carbonate solution. The ether phase was dried over MgSO₄, filtered and evaporated to dryness to give a crystalline residue. The residue was dissolved in ethanol which was acidified with ethanolic sulphuric acid to pH 5.5. After evaporation, the residue was recrystallized from isopropanol/ethyl ether. The identity of the product was confirmed with NMR.

Yield: 1.4 g

HPLC: 99.3% purity

SO₄²⁻: 97%

NMR (CDCl₃) δppm: 1.36 18H (s); 1.5–4.0 9H (broad m); 5.65 1H (m); 7.65 11H (m).

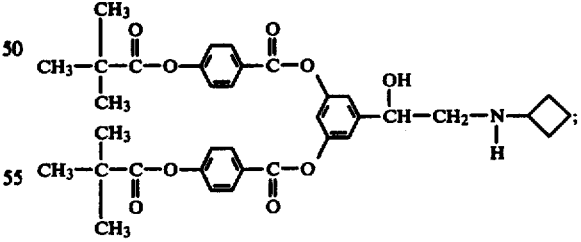

The 3',5'-bis-(4-pivaloyloxybenzoyloxy)-2-cyclobutylamino acetophenone hydrochloride which was used as starting material was prepared as follows.

3',5'-Bis-(4-pivaloyloxybenzoyloxy)-2-cyclobutylamino acetophenone hydrochloride A solution of 5.1 g (0.008 moles) of 3',5'-bis-(4-pivaloyloxybenzoyloxy)-2-bromo-acetophenone and 2.7 g (0.017 moles) of N-benzyl-cyclobutylamine in 100 ml of dry acetone was boiled under reflux and stirring for 18 hrs. After filtering and evaporation to dryness, the residue was dissolved in ethyl ether to which then 2 N HCl was added under stirring.

The ether phase was separated, washed with 2 N HCl and evaporated to dryness to yield 5 g of a red-brown oily residue. This oil was dissolved in 100 ml of acetone and hydrogenated in the presence of 0.5 g 10% Pd/C at an ambient temperature and pressure for 1 h. A precipitate was formed during the hydrogenation which was dissolved by addition of ethanol. The catalyst was then filtered off and the filtrate evaporated. The residue crystallized from acetone, and this material was further recrystallized from ethanol/diethyl ether. The identity of the product was confirmed with NMR.

Yield: 2.2 g

NMR (CDCl₃) δppm: 1.40 18H (s); 1.4–4.3 7H (broad m); 4.65 2H (s); 7.65 11H (m).

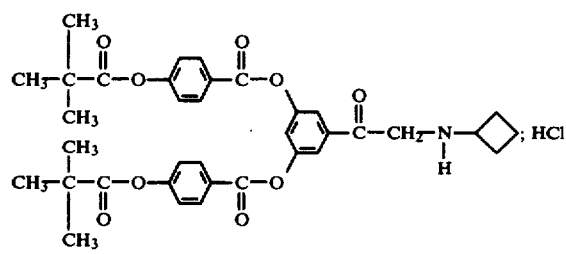

EXAMPLE 7

Preparation of 1-[3,5-bis-(4-pivaloyloxybenzoyloxy)phenyl]-2-(1-methyl)-cyclobutylaminoethanol sulphate A solution of 3',5'-bis-(4-pivaloyloxybenzoyloxy)-2-N-benzyl-(1-methyl)cyclobutylamino acetophenone hydrochloride in 100 ml of ethanol was hydrogenated at 50° C. and 345 kPa (50 psig) in the presence of 0.3 g 10% Pd/C for 18 hrs. The catalyst was then filtered off and the filtrate evaporated to dryness. The crystalline residue was recrystallized from 25 ml of dry ethyl ether to yield 0.3 g of a compound found to be of 79.2% purity by HPLC analysis. The filtrate was thereafter evaporated to dryness, and the residue made alkaline with sodium carbonate solution which was then extracted with ethyl ether. The ether phase was evaporated and the residue taken up in ethanol and acidified with ethanol to pH 5.5. This solution was then evaporated, and the residue was dissolved in 20 ml of warm isopropanol and left to crystalline. The first crystalline fraction isolated, 0.3 g, was found to be of 91% purity by HPLC, and the second fraction, 0.1 g, was found to be of 94.4% purity by HPLC and contained 96% of the calculated $SO_4^{2-}$. The identity of the product was confirmed with NMR.

NMR (DMSO) δppm: 1.16 21H (s); 1.55 6H (m); 2.33 (DMSO); 2.72 2H (m); 4.80 1H (m); 7.68 11H (m).

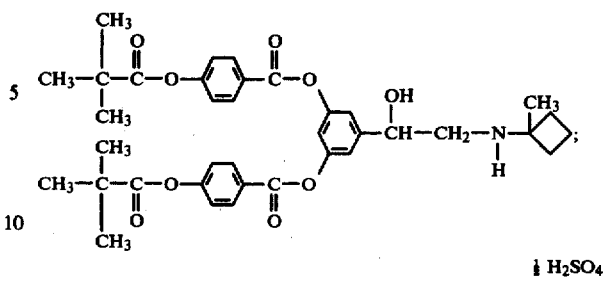

The 3',5'-bis-(4-pivaloyloxybenzoyloxy)-2-N-benzyl-(1-methyl)-cyclobutylamino acetophenone hydrochloride which was used as starting material was prepared as follows.

3',5'-bis-(4-pivaloyloxybenzoyloxy)-2-N-benzyl-(1-methyl)-cyclobutylamino acetophenone hydrochloride A solution of 8.9 g (0.014 moles) of 3',5'-bis-(4-pivaloyloxybenzoyloxy)-2-bromo-acetophenone and 5.3 g (0.03 moles) of N-benzyl-1-methyl-cyclobutylamine in 200 ml of acetone was boiled under reflux for 18 hrs. After evaporation in vacuo, ethyl ether was added to the residue whereby N-benzyl-1-methylcyclobutylamine hydrobromide precipitated (3.1 g). After filtering, the filtrate was acidified with ethanolic hydrochloric acid whereby the title compound precipitated. The precipitate was filtered off and washed with water. The identity of the product was confirmed with NMR.

Yield: 3.0 g (33%)

NMR (CDCl₃, TMS) δppm: 1.30 18H (s); 1.70 7H (m); 2.70 2H (m); 3.83 2H (t); 4.50 2H (m); 7.75 16H (m).

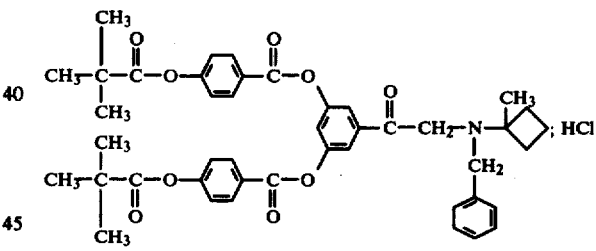

EXAMPLE 8

Preparation of 1-[3,5-bis-(4-carboxymethyl-banzoyloxy)phenyl]-2-tert.butylamino ethanol hydrochloride A solution of 1.5 g of 3',5'-bis-(4-carboxymethylbenzoyloxyphenyl)-2-N-benzyl-t-butylaminoacetophenone in 50 ml of ethanol was hydrogenated in the presence of 0.2 g 10% Pd/C at 345 kPa (50 psi) and 50° C. for 24 h. After filtering off the catalyst the filtrate was evaporated to dryness and the crystalline residue recrystallized from isopropanol. The identity of the product was confirmed with NMR.

Yield: 0.3 g. HPLC: 97.5%. Cl⁻ calculated: 6.05%.

− found: 5.7%.

NMR δppm: 0.9 9H (s); 2.8 2H (m); 3.45 6H (s); 4.25 (CD₃OH); 4.55 1H (m); 6.8 3H (m); 7.7 8H (m). (CD₃OD).

The compound used as starting material was prepared as follows.

(8a) Preparation of 3,5-bis-(4-carboxymethylbenzoyloxyphenyl)-acetophenone

A solution of 5.7 g 3,5-dihydroxyacetophenone and 15.0 g p-carboxymethylbenzoylchloride in 200 ml of pyridine was stirred at 60° C. for 24 hours. After evaporation the residue was dissolved in diethyl ether and washed with water. The ether phase was dried over magnesium sulphate, filtered and evaporated. The crystalline residue was recrystallized from ethanol. Yield: 9.5 g. NMR δppm: 2.65 3H (s); 4.05 6H (s); 7.75 3H (m); 8.30 8H (m). ($CDCl_3$+TMS).

(8b) Preparation of 3′,5′-bis-(4-carboxymethylbenzoyloxyphenyl)-2-bromoacetophenone To a solution of 9.4 g of the acetophenone obtained in step (a) in 100 ml of chloroform and 100 ml of dioxan is added dropwise with stirring 1.1 ml of bromine. The mixture is stirred for 2 hours at ambient temperature whereafter it is evaporated to dryness. The residue is dissolved in ethanol from which the title compound crystallizes.

Yield: 7.7 g.

NMR δppm: 4.10 6H (s); 4.60 2H (s); 7.95 3H (m); 8.35 8H (m). ($CDCl_3$ +TMS).

(8c) Preparation of 3′,5′-bis-(4-carboxymethylbenzoyloxyphenyl)-2-N-benzyl-t-butylaminoacetophenone A solution of 6.0 g of the bromoketone obtained in step (b) and 3.52 g of N-benzyl t-butylamine in 100 ml of acetone was boiled under reflux and stirring for 18 hours. After evaporation of the acetone the residue is extracted with diethyl ether. To the combined ether extracts is then added 2-N HCl and a light yellow oil separates. This oil is isolated and dissolved in ethanol and the title compound crystallizes upon addition of diethyl ether.

Yield 1.5 g. NMR δppm: 1.65 9H (s); 4.00 6H (s); 4.60 2H (m); 4.95 2H (m); 7.50 8H (m); 8.10 8H (m). ($CDCl_3$ +$CD_3OD$+TMS).

The following examples illustrate how the compounds of the invention can be incorporated in pharmaceutical compositions:

EXAMPLE 9

Aerosol for inhalation

| | |
|---|---|
| 1-[3,5-bis-(4-pivaloyloxybenzoyloxy)phenyl]-2-t-butyl-amino ethanol hydrochloride | 0.75 g |
| Miglyol ® | 0.20 g |
| Frigen ® 11/12/113/114 | ad 100.0 g |

EXAMPLE 10

Tablets

Each tablet contains:

| | |
|---|---|
| 1-[3,5-bis-(4-pivaloyloxybenzoyloxy)phenyl]-2-t-butyl-amino ethanol hydrochloride | 6.0 mg |
| Maize starch | 25.0 mg |
| Lactose | 206.0 mg |
| Gelatin | 1.5 mg |
| Talc | 10.0 mg |
| Magnesium stearate | 1.5 mg |
| | 250.0 mg |

EXAMPLE 11

Suppositories

Each suppository contains:

| | |
|---|---|
| 1-[3,5-bis-(4-pivaloyloxybenzoyloxy)phenyl]-2-t-butyl-amino ethanol hydrochloride | 6.0 mg |
| Ascorbyl palmitate | 1.0 mg |
| Suppository base (Imhausen H) | ad 2.000.0 mg |

EXAMPLE 12

Syrup

| | |
|---|---|
| 1-[3,5-bis-(4-pivaloyloxybenzoyloxy)phenyl]-2-t-butyl-amino ethanol hydrochloride | 0.060 g |
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified colour | 0.015 g |
| Purified water | ad 100.0 ml |

EXAMPLE 13

Inhalation solution

| | |
|---|---|
| 1-[3,5-bis-(4-pivaloyloxybenzoyloxy)phenyl]-2-t-butylamino ethanol hydrochloride | 0.75 g |
| Sodium pyrosulfite | 0.10 g |
| Disodium edetate | 0.10 g |
| Sodium chloride | 0.85 g |
| Purified water | ad 100.0 ml |

EXAMPLE 14

Solution for rectal administration (Rectal vials)

| | |
|---|---|
| 1-[3,5-bis-(4-pivaloyloxybenzoyloxy)phenyl]-2-t-butyl-amino ethanol hydrochloride | 6.0 mg |
| Sodium pyrosulfite | 1.5 mg |
| Disodium edetate | 0.3 mg |
| Sterile water | ad 3.0 ml |

EXAMPLE 15

Sublingual tablets

| | |
|---|---|
| 1-[3,5-bis-(4-pivaloyloxybenzoyloxy)phenyl]-2-t-butyl-amino ethanol hydrochloride | 3.0 mg |
| Lactose | 83.0 mg |
| Agar | 5.0 mg |
| Talc | 5.0 mg |
| | 100.0 mg |

EXAMPLE 16

Drops

| | |
|---|---|
| 1-[3,5-bis(4-pivaloyloxybenzoyl-oxy)phenyl-2-t-butyl-amino ethanol hydrochloride | 0.60 g |
| Ascorbic acid | 1.00 g |
| Sodium pyrosulfite | 0.10 g |
| Disodium edetate | 0.10 g |
| Liquid glucose | 50.00 g |
| Absolute alcohol | 10.00 g |
| Purified water | ad 100.0 ml |

EXAMPLE 17

Tablets

Each tablet contains:

| | |
|---|---|
| 1-[3,5-bis-(4-pivaloyloxybenzoyl-oxy)phenyl]2-t-butyl-amino ethanol hydrochloride | 6.0 mg |
| 1-(3',5'-dihydroxyphenyl)-2-t-butylaminoethanol sulphate (terbutaline) | 2.0 mg |
| Maize starch | 25.0 mg |
| Lactose | 204.0 mg |
| Gelatin | 1.5 mg |
| Talc | 10.0 mg |
| Magnesium stearate | 1.5 mg |
| | 250.0 mg |

EXAMPLE 18

Tablets

Each tablet contains:

| | |
|---|---|
| 1-[3,5-bis-(4-pivaloyloxybenzoyl-oxy)phenyl]-2-t-butyl-amino ethanol hydrochloride | 6.0 mg |
| α-(tert.)-butylaminomethyl-4-hydroxy-m-xylene-α'-diolsulphate (salbutamol) | 2.0 mg |
| Maize starch | 25.0 mg |
| Lactose | 204.0 mg |
| Gelatin | 1.5 mg |
| Talc | 10.0 mg |
| Magnesium stearate | 1.5 mg |
| | 250.0 mg |

EXAMPLE 19

Tablets

Each tablet contains:

| | |
|---|---|
| 1-[3,5-bis-(4-pivaloyloxybenzoyl-oxy)phenyl]-2-t-butyl-amino ethanol hydrochloride | 6.0 mg |
| 1-(3',5'-diisobutyryloxy-phenyl)-2-(t-butyl-amino)-ethanol, hydrochloride (ibuterol) | 2.0 mg |
| Maize starch | 25.0 mg |
| Lactose | 204.0 mg |
| Gelatin | 1.5 mg |
| Talc | 10.0 mg |
| Magnesium stearate | 1.5 mg |
| | 250.0 mg |

EXAMPLE 20

Tablets

Each tablet contains:

| | |
|---|---|
| 1-[3,5-bis-(4-pivaloyloxybenzoyl-oxy)phenyl]-2-t-butyl-amino ethanol hydrochloride | 6.0 mg |
| 1-(3',5'-dihydroxyphenyl)-2-(i-propylamino)-ethanol sulphate (orciprenaline) | 2.0 mg |
| Maize starch | 25.0 mg |
| Lactose | 202.0 mg |
| Gelatin | 1.5 mg |
| Talc | 10.0 mg |
| Magnesium stearate | 1.5 mg |
| | 250.0 mg |

EXAMPLE 21

Syrup

| | |
|---|---|
| 1-[3,5-bis-(4-pivaloyloxybenzoyl-oxy)phenyl]-2-t-butyl-amino ethanol hydrochloride | 0.060 g |
| 1-(3',5'-dihydroxyphenyl)-2-(t-butyl-amino)-ethanol sulphate (terbutaline) | 0.020 g |
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified colour | 0.015 g |
| Purified water | ad 100.0 ml |

Pharmacological tests

A. Duration of serum levels of terbutaline after administration of compounds of the invention to unanaesthetized dogs

Test Method

Method

Five dogs (Beagle, ♂, 13–18 kg) have been used repeatedly in the study. Each dog was used at most once a week. Food was withheld from the animals the night before the experiment (water ad libitum). The test compound was solved or suspended in 8 ml of distilled water, and delivered into the back of the mouth by use of a syringe and a short tube. This oral supply was followed by a water rinse of 8 ml.

The blood was collected from the cephalic veins in the forelegs by use of evacuated tubes. The esterase inhibitor diisopropylfluophosphate (DFP) was added, the samples centrifugated (+5°) and the most amount of terbutaline in plasma determined by a massfragmentographic analysis method. The serum level of terbutaline indicates the degree of bronchospasmolytic effect of the test compounds but does not account for the intrinsic bronchospasmolytic effect exhibited by the test compounds.

The amounts of the test substances to be administered were selected so that the level of terbutaline, when administered per se, corresponds to the serum levels obtained and found effective in patients at clinical use, that is a level of terbutaline of at least 2 ng/ml serum for 6 to 8 hours. The doses of the test substances of the invention were selected so that the serum levels of terbutaline obtained would correspond approximately with the serum levels obtained after administration of terbutaline per se.

Test Results

The test results are given in Table 1 below, where the time course of the serum level of terbutaline in the test animals is given. Each set of serum levels is the result of test in one dog. The boxed time interval represents the interval where a clinically effective serum level of terbutaline is obtained. Thus, the boxed interval represents the clinically useful duration of the test compounds.

volume of 0.75 ml/100 g body weight. Intratracheal pressure (insufflation pressure) was measured by use of a T-junction on the tracheal cannula connected to a Statham pressure transducer P23BC. An increase in intratracheal pressure, indicating bronchoconstriction, was elicited by i.v. injection (v. jugularis) of histamine. The constricting agent was injected every 10 minutes by a timer-controlled perfusor in a dose giving about 80% of the maximum contractile response ($1-2 \cdot 10^{-8}$ mol/kg). The bronchospasmolytic drugs to be tested were solved in aq. dest. containing 3% glycerol and nebulized by use of a Bird Inline Nebulizer (air pressure

TABLE 1

Serum levels ng/ml of terbutaline after p.o administration of terbutaline and various terbutaline esters to dogs Test compound:

$$R^1O-C_6H_3(OR^2)-CH(OH)-CH_2-NH-C(CH_3)_3$$

| Compound No. | $R^1$ | $R^2$ | Administered amount of test substance (mg/kg) | Serum level of terbutaline (ng/ml) obtained after (hours after administration) |
|---|---|---|---|---|
| | | | | 1  2  3  4  6  8  12  16  24 |
| | H | H (terbutaline, reference) | 0.1 | [5.7 13.7 9.2 6.1 3.4 2.2] 1.1 0.8 0.35 |
| | H | H | 0.03 | [4.8 2.9 2.4 2.2 1.9] (not measured) |
| I | $(CH_3)_3C-C(O)-O-C_6H_4-C(O)-$ | $(CH_3)_3C-C(O)-O-C_6H_4-C(O)-$ | 0.6 | 0.2 1.0 [3.0 5.8 6.3 4.9 3.1 1.9] 0.8 |

It is seen in Table 1 that the test substance of the invention gives a serum level of 2 ng/ml or more for about 16 hours. The reference substance terbutaline gives a corresponding serum level for about 8 hours, which is the duration normally obtained at clinical use of terbutaline. The serum level of terbutaline indicates the degree of bronchospasmolytic effect of the test compounds but does not account for the intrinsic bronchospasmolytic effect of the test compounds.

B. Duration of bronchospasmolytic activity after local administration via aerosol

Test method

Guinea-pigs, strain Dunkin-Hartley, of either sex, weighing 500–900 g were anaesthetized by i.p. injection and i.v. infusion of pentobarbital. The animals were artifically ventilated with a Braun constant volume respiration pump giving 70 strokes/min and a stroke 0.2 MPa; droplet spectrum around 1 micron). The generated aerosol was lead through the respirator and tracheal cannula. Inhalation of drug was going on during periods of 30 min. The resulting bronchodilator effect was calculated from the percentage reduction of the histamine evoked rise of the insufflation pressure.

The concentration of the test substance in the solved composition that when nebulized produced 50% inhibition of the increased tracheal pressure (ED50) was measured. The duration of the bronchospasmolytic effect was measured at the ED50 dose level by the time after inhalation it took for the test animal to recover 80% of the initial bronchocontractile value.

Twentysix guinea-pigs were used in the test.

Test results

The test results are given in Table 2 below.

TABLE 2

Duration of bronchospasmolytic activity after local administration via aerosol.

Test compound:

$$R^1O-C_6H_3(OR^2)-CH(OH)-CH_2-NH-C(CH_3)_3$$

| Compound No. | $R^1$ | $R^2$ | Concentration of test substance that gives 50% inhibition of increased tracheal pressure ED50 (mol/l) | Duration of bronchospasmolytic effect at ED50 concentration (relative values terbutaline = 1) |
|---|---|---|---|---|
| | H | H (terbutaline reference) | $2.6 \cdot 10^{-4}$ | 1 |

TABLE 2-continued

Duration of bronchospasmolytic activity after local administration via aerosol.

| Compound No. | Test compound $R^1O$-phenyl-CH(OH)-CH$_2$-NH-C(CH$_3$)$_3$ with $R^2O$ | | Concentration of test substance that gives 50% inhibition of increased tracheal pressure ED50 (mol/l) | Duration of bronchospasmolytic effect at ED50 concentration (relative values terbutaline = 1) |
|---|---|---|---|---|
| | $R^1$ | $R^2$ | | |
| I | $(CH_3)_3C-\overset{O}{\underset{\|}{C}}-O-\text{phenyl}-\overset{O}{\underset{\|}{C}}-$ | $(CH_3)_3C-\overset{O}{\underset{\|}{C}}-O-\text{phenyl}-\overset{O}{\underset{\|}{C}}-$ | $4.5 \cdot 10^{-4}$ | 3 |

It is seen in Table 2 that the duration of bronchospasmolytic effect of Compound I of the invention at local administration via aerosol at ED50 dose level is about three times longer than the duration of the reference substance terbutaline. It is also seen that the ED50 for Compound I of the invention was higher than ED50 for terbutaline, or $4.5 \cdot 10^{-4}$ mol/l vs. $2.6 \cdot 10^{-4}$ mol/l.

It was also noted at the test that Compound I gave an onset of effect comparable to that produced by terbutaline.

No significant effect was noted on the cardiovascular system from the inhaled drugs in the concentrations used.

C. Bronchodilating effect of the compounds of the invention per se

C1. In vitro test on isolated guinea-pig trachea

Test method

The trachea from guinea-pigs was dissected out, cut spirally and transferred to a 10 ml organ bath containing Krebs solution of 37° and aerated with carbogen. The tracheal strip was contracted by pilocarpine ($4 \cdot 10^{-6}$ mol/l) producing a tension of about 1.5 g. Isometric recording was made by use of a transducer FTO3 and a Grass polygraph 7D. Before the administration of the test compound the esterase inhibitor eserin was added to the bath in a concentration of $1 \cdot 10^{-6}$ mol/l. The concentration of the test substances which produces 50% relaxation (EC50) of the pilocarpine contracted trachea was recorded as well as potentiating or inhibiting influence of the test substances of the invention on the relaxing effect of terbutaline. In this last mentioned test the muscle preparation was pretreated with the test compounds during 5 minutes, before the response of terbutaline was recorded.

Test results

The test results are given in Table 3 below.

TABLE 3

Bronchodilating effect on isolated tracheal muscle from guinea-pig

| Compound No. | Test compound $R^1O$-phenyl-CH(OH)-CH$_2$-NH-C(CH$_3$)$_3$ with $R^2O$ | | Concentration of test substance producing 50% relaxation of the trachea (EC50) ($10^{-7}$ moles/l) | Number of tests | Potentiating or inhibiting effect of the test substance on the bronchodilating effect of terbutaline |
|---|---|---|---|---|---|
| | $R^1$ | $R^2$ | | | |
| | H | H (terbutaline reference) | $2.1 \pm 0.5$ | 6 | — |
| II | $\underset{CH_3}{\overset{CH_3}{\underset{\|}{\overset{\|}{HC}}}}-\overset{O}{\underset{\|}{C}}-O-\text{phenyl}-\overset{O}{\underset{\|}{C}}-$ | $\underset{CH_3}{\overset{CH_3}{\underset{\|}{\overset{\|}{HC}}}}-\overset{O}{\underset{\|}{C}}-O-\text{phenyl}-\overset{O}{\underset{\|}{C}}-$ | $18 \pm 6$ | 5 | none |
| I | $(CH_3)_3C-\overset{O}{\underset{\|}{C}}-O-\text{phenyl}-\overset{O}{\underset{\|}{C}}-$ | $(CH_3)_3C-\overset{O}{\underset{\|}{C}}-O-\text{phenyl}-\overset{O}{\underset{\|}{C}}-$ | $18 \pm 6$ | 5 | none |

It is seen in Table 3 that both the test substances I and II produce a bronchodilating effect at about $1.8 \cdot 10^{-6}$ mol/l, that is in a concentration range about 9 times higher than that concentration of the reference compound terbutaline which in this test produces normal dilation of the trachea. This intrinsic effect of the test substances I and II was not blocked by presence of the $\beta$-receptor blocking agent propranolol in a concentration of $3 \cdot 10^{-6}$ mol/l. The bronchodilating effect of terbutaline is, on the other hand, blocked by propranolol.

The intrinsic bronchodilating effect of the test compounds is an advantageous property which makes them particularly suitable for oral or local administration e.g. in aerosol form. This property makes the compounds suitable also for other administration forms such as by injection.

No potentiating or inhibiting activity of the test substances I and II on the bronchodilating effect of terbutaline was observed.

C2. Bronchospasmolytic effect of the test compounds after oral administration in guinea-pigs

Test method

Male guinea-pigs, Dunkin-Hartley strain, 150–200 g, were used in the study. The animals were starved for about 15 hours (water ad libitum) before the administration, by a stomach tube, of test compound or vehicle (controls). To establish an adequate time period between administration and histamine exposure, the maximum plasma level of terbutaline produced from the hydrolysis of the given pro-drugs of terbutaline was determined. Thus, blood samples (in pre-experimental series) were collected from guinea-pigs at different times after the administration of the test compound and the plasma level of terbutaline was determined by a massfragmentographic assay. A peak in the plasma terbutaline was noted 50-60 minutes after the administration, and this time was selected as time for start of histamine exposure.

The histamine aerosol was generated by Bird inline nebulizers from a solution containing 0.02% histamine-HCl and 3% glycerole. The protecting effect was estimated from the delay in appeareance of signs of anoxia in drug-treated animals. Of the controls >90% showed respiratory distress within 3 minutes in the used aerosol. Drug-treated guinea-pigs without any signs of respiratory influence from the histamine during these first 3 minutes were denoted as protected.

Test results

The test results are given in Table 4 below.

bronchospasm. This is due to the intrinsic bronchospasmolytic effect of the test compounds.

D. Effect of the test compounds on isolated heart preparations

D1. In vitro test on isolated guinea-pigs auricles

Test method

Male guinea-pigs strain Dunkin Hartley (400–500 g) were used. After bleeding and removal of the heart the auricles were dissected free from the ventricular part and submerged into carbogen aerated Krebs solution of 37°. The frequency and force of the spontaneously beating preparation was recorded by a Grass transducer FTO3. In the polygraph (Grass 7D) the signals from the isometric transducer passed a trigger function from the drive amplifier to the tachograph to record the rate.

The esterase inhibitor eserine was added to a concentration of $1.10^{-6}$ mol/l in the organ bath before the drugs to be tested were added. The intrinsic activity of the test compounds on the heart preparation, that is their effect on heart rate (chronotropic effect) and their effect on the force of the heart beats (inotropic effect), and their possible interaction with terbutaline was studied.

Test results

TABLE 4

Protecting effect of the test substances against histamine-induced bronchospasm in unanaesthtized guinea-pigs Test compound: R¹O-C₆H₃(OR²)-CH(OH)-CH₂-NHC(CH₃)₃

| Compound No. | R¹ | R² | Dose protecting 50% of the test animals for more than 3 minutes (ED50) mg/kg | mmole/kg |
|---|---|---|---|---|
|  | H | H (terabutaline, reference) | 0.4 | $1.5 \cdot 10^{-3}$ |
| I | (CH₃)₃C—C(O)—O—C₆H₄—C(O)— | (CH₃)₃C—C(O)—O—C₆H₄—C(O)— | 1.1 | $1.6 \cdot 10^{-3}$ |
| II | (CH₃)₂CH—C(O)—O—C₆H₄—C(O)— | (CH₃)₂CH—C(O)—O—C₆H₄—C(O)— | 1.1 | $1.6 \cdot 10^{-3}$ |

It is seen in Table 4 that the test compound I and II on molar basis were about equally effective as terbutaline, in protecting the test animals against histamine-induced The test results are given in Table 5 below.

TABLE 5

Effect of the test substances on isolated auricles from guinea-pig heart

Test compound: R¹O-C₆H₃(OR²)-CH(OH)-CH₂-NH-C(CH₃)₃

| Compound No. | R¹ | R² | Effect on isolated auricle inotropic effect | chromotropic effect |
|---|---|---|---|---|
|  | H | H (terabutaline, reference) | 1.0 | 1.0 |
| I | (CH₃)₃C—C(O)—O—C₆H₄—C(O)— | (CH₃)₃C—C(O)—O—C₆H₄—C(O)—O— | 0 | 0 |

(relative values)

TABLE 5-continued

Effect of the test substances on isolated auricles from guinea-pig heart

Test compound:

$R^1O-C_6H_3(OR^2)-CH(OH)-CH_2-NH-C(CH_3)_3$

| Compound No. | $R^1$ | $R^2$ | Effect on isolated auricle inotropic effect | chromotropic effect |
|---|---|---|---|---|
| | | | (relative values) | |
| II | $HC(CH_3)_2-C(=O)-O-C_6H_4-C(=O)-$ | $HC(CH_3)_2-C(=O)-O-C_6H_4-C(=O)-$ | 0 | 0 |

It is seen in Table 5 that none of the test compounds I and II showed any chronotropic or inotropic effect.

The possible potentiating or inhibiting response of the test compounds I and II on the chronotropic and inotropic effect of terbutaline was also investigated by adding the test compounds I and II to the organ bath in the same concentration as terbutaline. No potentiating or inhibiting effect on the chronotropic and inotropic effect of terbutaline was observed for any of the test compounds I and II.

D2. In vivo test on the effect of the test compounds on the heart rate in dogs

Test method

Five dogs (Beagle, ♂, 13–18 kg) have been used repeatedly in the study. Each dog was used at most once a week. Food was withheld from the animals the night before the experiment (water ad libitum). The test compound was solved or suspended in 8 ml of distilled water, and delivered into the back of the mouth by use of a syringe and a short tube. This oral supply was followed by a water rinse of 8 ml.

The blood was collected from the cephalic veins in the forelegs by use of evacuated tubes. The esterase inhibitor diisopropylfluophosphate (DFP) was added, the samples centrifugated (+5°) and the amount of terbutaline in plasma determined by a massfragmentographic analysis method. The serum level of terbutaline indicates the degree of bronchospasmolytic effect of the test compounds, provided terbutaline is solely responsible for the bronchospasmolytic effect. This method does, however, not measure the intrinsic activity of the test compounds.

The amounts of the test substances to be administered were selected so that the level of terbutaline, when administered per se, corresponds to the serum levels obtained and found effective in patients at clinical use, that is a level of terbutaline of at least 2 ng/ml serum for 6 to 8 hours. The doses of the test substances of the invention were selected so that the serum levels of terbutaline obtained would correspond approximately with the serum levels obtained after administration of terbutaline per se.

The heart rate was determined by a stethoscope (the mean of three determinations during a 5-minute periode) before the administration of drug and before each blood sampling.

Test result

The relative effect of the test compounds on the heart rate of the test animals was illustrated by plotting in a diagram the increase in heart rate measured at a certain serum concentration of terbutaline versus the logarithm of the said terbutaline concentration in serum. Only values before and up to the maximal increase in heart rate were used. This method will produce a graph consisting of a substantially straight line. When such a line is drawn for each test compound, it can be seen from the slope of the line how the heart rate is correlated to the serum concentration of the test compound.

In this test, the slope of the line and the coefficient of correlation was investigated for the reference substance terbutaline and for test compound No. I. The results are given in Table 6.

TABLE 6

The influence of the test compounds on the heart rate in dogs

Test compound:

$R^1O-C_6H_3(OR^2)-CH(OH)-CH_2-NH-C(CH_3)_3$

| Compound No. | $R^1$ | $R^2$ | Tested dosage range (mg/kg) | Slope of the line increase in heart rate vs. logarithm of corresponding serum conc. | Correlation coefficient | Number of measurements |
|---|---|---|---|---|---|---|
| | H | H (reference) | 0.01–0.1 | 1.04 | 0.9598 | 12 |
| I | $(CH_3)_3C-C(=O)-O-C_6H_4-C(=O)-$ | $(CH_3)_3C-C(=O)-O-C_6H_4-C(=O)-$ | 0.3–2.7 | 0.53 | 0.9764 | 6 |

It is seen in Table 6 that the test compound I produces a relatively much lower increase in heart rate than the reference compound terbutaline.

Comments to the test results from the pharmacological tests

It will first be noted that the compounds of the invention are hydrolysed in serum and body fluids producing the compound terbutaline, which then exerts its bronchodilating effect. That such a hydrolysis takes place is indirectly obvious from the reported pharmacological tests, where the serum levels etc. of terbutaline consistently have been measured.

It is shown in test A that compound I of the invention gives a clinically useful serum level of terbutaline (2 ng/ml serum, or higher) during a time period which is at least twice as long as the time period during which the reference substance terbutaline gives a corresponding serum level (16 hours versus 8 hours).

Test B shows that Compound I of the invention at local administration via aerosol at ED50 doses gives a duration of effect which is three times longer than the duration of terbutaline.

In test C1 (bronchodilating effect in vitro in isolated guinea-pig trachea) it is demonstrated that the test compounds I and II exert a certain intrinsic bronchodilating effect. This bronchodilatng effect is, in contrast to what is the case with terbutaline, not inhibited by the β-receptor blocking agent propranolol. The intrinsic bronchodilating effect of the compounds of the invention is an added advantageous property which makes the compounds of particular interest for local administration to the lungs e.g. in aerosol form, or for oral administration. The intrinsic effect makes the compounds suitable also for other administration forms such as by injection.

Test C2 demonstrates the bronchospasmolytic effect of the test compounds I and II in in vivo test in guinea-pigs. The bronchospasmolytic activity of the test compounds at oral administration is on molar basis about equal with the activity of the reference compound terbutaline. This indicates that the intrinsic activity of the test compounds is of practical value.

In test D1 it is demonstrated in in vitro test that the test compounds of the invention per se have no inotropic or chronotropic effect on isolated guinea-pig heart preparation. The esterase inhibitor is added to make sure that it is the intrinsic effect of the test compounds-which are esters-that is measured, and not the effect of the hydrolysis product terbutaline.

Test D2 demonstrates by an in vivo test in dogs that the test compound I of the invention has a considerably reduced stimulating effect on the heart rate compared with the heart rate stimulating effect of terbutaline.

In conclusion, the compounds of the invention are bronchospasmolytic agents having an exceedingly long duration of action, and a rapid onset of effect at local administration via aerosol. They exhibit in addition reduced heart effects compared to the prior art compound terbutaline. They exhibit also an intrinsic bronchospasmolytic effect.

The long duration of activity, measured as the time period during which the serum level of the hydrolysis product terbutaline is at least 2 ng/ml or higher, means that the compounds of the invention will make it possible to reduce the number of times per 24 hours that asthmatic patients have to take their medication. In particular, a duration of therapeutic activity of about 16 hours will make it possible to protect the patients effectively and with less side-effects during normal periods of sleep with one single dose of the active substance.

What we claim is:

1. A compound of the formula

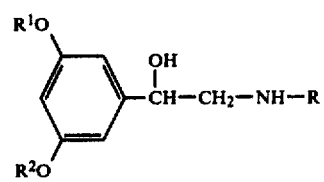

and therapeutically acceptable salts thereof, in which formula R, $R^1$ and $R^2$ are as follows:

R is selected from the group consisting of —$C(CH_3)_3$,

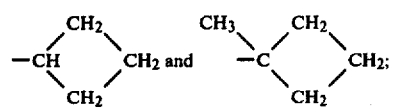

$R^1$ is selected from the group consisting of H and $R^2$;
$R^2$ is selected from the group consisting of

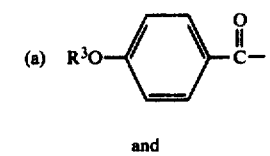

and

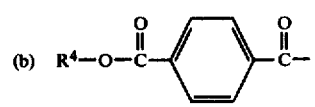

in which formulas
$R^3$ is selected from the group consisting of
(a) H;

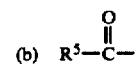

wherein $R^5$ is a straight or branched alkyl group containing 1-4 carbon atoms;

and

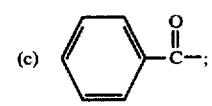

and wherein
$R^4$ is selected from the group consisting of
(b) an alkyl group containing 1-3 carbon atoms.

2. A compound according to claim 1, and therapeutically acceptable salts thereof, in the form of a substantially pure optical isomer.

3. A compound according to claim 1, and therapeutically acceptable salts thereof, wherein $R^1$ and $R^2$ both are

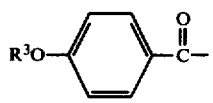

wherein R³ is as defined in claim 1.

4. A compound according to claim 1, and therapeutically acceptable salts thereof, wherein R¹ is H and R² is

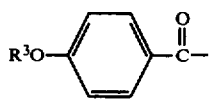

wherein R³ is as defined in claim 1.

5. A compound according to any of claims 1-4 wherein R is —C(CH₃)₃.

6. A compound according to claim 1, and therapeutically acceptable salts thereof, of the formula

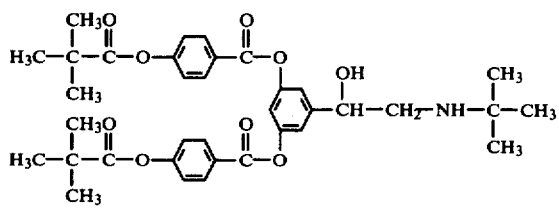

7. A compound according to claim 1, and therapeutically acceptable salts thereof, of the formula

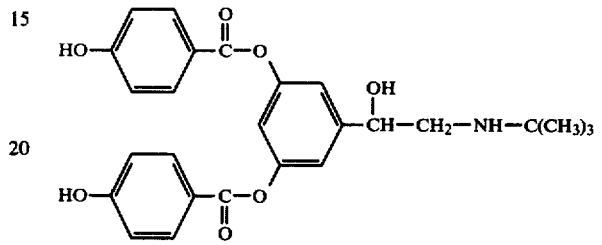

8. A compound according to claim 1, and therapeutically acceptable salts thereof, of the formula

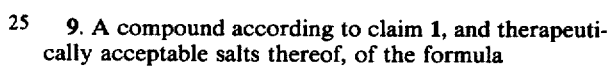

9. A compound according to claim 1, and therapeutically acceptable salts thereof, of the formula

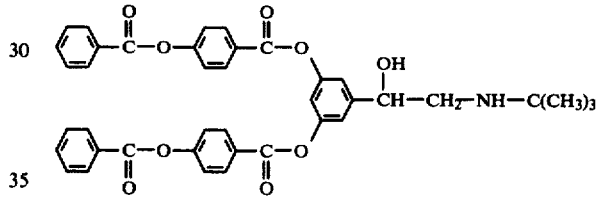

10. A compound according to claim 1, and therapeutically acceptable salts thereof, of the formula

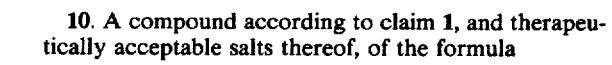

11. A compound according to claim 1, and therapeutically acceptable salts thereof, of the formula

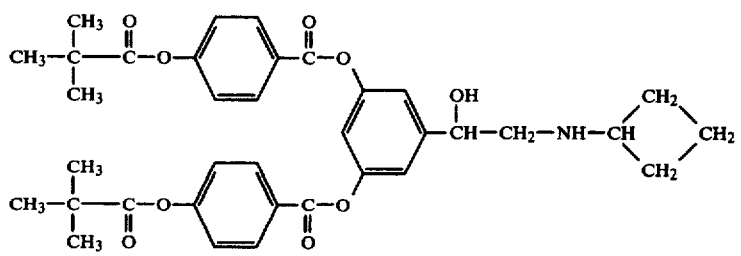

12. A pharmaceutical preparation comprising as active ingredient an effective amount of a compound according to any of claims 1-11, optionally in association with a pharmaceutically acceptable carrier.

13. A pharmaceutical preparation according to claim 12 in dosage unit form.

14. A pharmaceutical preparation comprising as active ingredients a first component comprising a compound according to any of claims 1-11 in combination with a second component comprising a conventionally used bronchospasmolytic agent having rapid onset of action.

15. A pharmaceutical preparation according to claim 14 wherein the said second component is selected from the group consisting of terbutaline, ibuterol, orciprenaline, salbutamol, epinephrine, isoprenaline, and ephedrine.

16. A method for producing bronchodilation in mammals including man, characterized by administering to a host in need of such treatment a therapeutically effective amount of a compound according to any of claims 1-11.

17. A method according to claim 16, characterized by administering a compound according to claim 6.

18. A method for producing relaxation of the human uterus, characterized by administering to a host in need of such treatment an effective amount of a compound according to any of claims 1-11.

19. A method according to claim 18, characterized by administering a compound according to claim 6.

* * * * *